US010265440B2

United States Patent
James et al.

(10) Patent No.: US 10,265,440 B2
(45) Date of Patent: Apr. 23, 2019

(54) POLYMERIC MATERIALS INCLUDING A GLYCOSAMINOGLYCAN NETWORKED WITH A POLYOLEFIN-CONTAINING POLYMER

(71) Applicant: COLORADO STATE UNIVERSITY RESEARCH FOUNDATION, Fort Collins, CO (US)

(72) Inventors: Susan P. James, Bellvue, CO (US); Susan S. Yonemura, Fort Collins, CO (US); Ariane Vartanian, Santa Clara, CA (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 3 days.

(21) Appl. No.: 15/467,756

(22) Filed: Mar. 23, 2017

(65) Prior Publication Data

US 2017/0189583 A1    Jul. 6, 2017

Related U.S. Application Data

(63) Continuation-in-part of application No. 14/506,932, filed on Oct. 6, 2014, which is a continuation of
(Continued)

(51) Int. Cl.
*A61L 27/52*    (2006.01)
*C08G 81/02*    (2006.01)
(Continued)

(52) U.S. Cl.
CPC ............ *A61L 27/52* (2013.01); *A61K 9/0024* (2013.01); *A61K 9/06* (2013.01); *A61K 31/726* (2013.01);
(Continued)

(58) Field of Classification Search
CPC ....................................................... A61L 27/52
(Continued)

(56) References Cited

U.S. PATENT DOCUMENTS 6,833,488 B2 * 12/2004 Bucevschi .............. A61L 15/60
524/17
2002/0193516 A1    12/2002 Bucevschi et al.
(Continued)

FOREIGN PATENT DOCUMENTS

WO          2008/130647 A1    10/2008
WO    WO-2008130647 A1 * 10/2008 ......... C08B 37/0063

OTHER PUBLICATIONS

International Search Report and Written Opinion issued in PCT/US2010/054745, dated Jul. 20, 2011.
(Continued)

*Primary Examiner* — Arrie L Reuther
(74) *Attorney, Agent, or Firm* — Heslin Rothenberg Farley & Mesiti P.C.

(57) ABSTRACT

The present invention relates to polymeric materials including a glycosaminoglycan networked with a polyolefin-containing polymer. The present invention also relates to hydrogels containing the polymeric materials. The present invention further relates to methods of synthesizing the polymeric materials and hydrogels of the present invention.

20 Claims, 10 Drawing Sheets

Batch-to-Batch Repeatability

Related U.S. Application Data application No. 13/503,900, filed as application No. PCT/US2010/054745 on Oct. 29, 2010.

(60) Provisional application No. 61/256,275, filed on Oct. 29, 2009.

(51) Int. Cl.
| | |
|---|---|
| *A61L 27/20* | (2006.01) |
| *A61L 27/18* | (2006.01) |
| *A61K 47/36* | (2006.01) |
| *A61L 15/60* | (2006.01) |
| *A61K 31/726* | (2006.01) |
| *A61K 31/727* | (2006.01) |
| *A61K 31/728* | (2006.01) |
| *A61K 31/737* | (2006.01) |
| *C08J 3/075* | (2006.01) |
| *C08F 251/00* | (2006.01) |
| *C08L 51/02* | (2006.01) |
| *A61K 9/00* | (2006.01) |
| *A61K 9/06* | (2006.01) |
| *A61K 47/32* | (2006.01) |

(52) U.S. Cl.
CPC .......... *A61K 31/727* (2013.01); *A61K 31/728* (2013.01); *A61K 31/737* (2013.01); *A61K 47/32* (2013.01); *A61K 47/36* (2013.01); *A61L 15/60* (2013.01); *A61L 27/18* (2013.01); *A61L 27/20* (2013.01); *C08F 251/00* (2013.01); *C08G 81/02* (2013.01); *C08J 3/075* (2013.01); *C08L 51/02* (2013.01); *A61L 2400/06* (2013.01); *A61L 2430/06* (2013.01); *A61L 2430/38* (2013.01); *C08G 2210/00* (2013.01); *C08J 2351/02* (2013.01)

(58) Field of Classification Search
USPC .......................................................... 524/58
See application file for complete search history.

(56) References Cited

U.S. PATENT DOCUMENTS

| | | | |
|---|---|---|---|
| 2003/0170308 A1* | 9/2003 | Cleary | A61L 15/60 424/486 |
| 2003/0236514 A1 | 12/2003 | Schwarz | |
| 2015/0031800 A1 | 1/2015 | James et al. | |

OTHER PUBLICATIONS

Supplementary European Search Report issued in application No. EP10830503, dated Sep. 26, 2013.

K. Salchert et al., "Fibrillar collagen assembled in the presence of glycosaminoglycans to constitute bioartificial stem cell niches in vitro" Journal of Materials Science: Materials in Medicine 16:581-585 (2005).

* cited by examiner ated as U.S. 2015-0031800 A1 on Jan. 29, 2015), which is a continuation of U.S. patent application Ser. No. 13/503,900, filed with the U.S. Patent and Trademark Office on Apr. 25, 2012 (published as U.S. 2012-0264852 A1 on Oct. 18, 2012), which is a U.S. National Phase filing under 35 U.S.C. § 371 of International Application No. PCT/US2010/054745, filed Oct. 29, 2010 (published as WO 2011/059819 on May 19, 2011), which claims priority to U.S. Provisional Patent Application Ser. No. 61/256,275, filed Oct. 29, 2009, the entire disclosures of which are hereby incorporated by reference herein in their entirety.

POLYMERIC MATERIALS INCLUDING A GLYCOSAMINOGLYCAN NETWORKED WITH A POLYOLEFIN-CONTAINING POLYMER

CROSS-REFERENCE TO RELATED APPLICATIONS

This application is a continuation-in-part application of U.S. patent application Ser. No. 14/506,932, filed on Oct. 6, 2014 (published as U.S. 2015-0031800 A1 on Jan. 29, 2015), which is a continuation of U.S. patent application Ser. No. 13/503,900, filed with the U.S. Patent and Trademark Office on Apr. 25, 2012 (published as U.S. 2012-0264852 A1 on Oct. 18, 2012), which is a U.S. National Phase filing under 35 U.S.C. § 371 of International Application No. PCT/US2010/054745, filed Oct. 29, 2010 (published as WO 2011/059819 on May 19, 2011), which claims priority to U.S. Provisional Patent Application Ser. No. 61/256,275, filed Oct. 29, 2009, the entire disclosures of which are hereby incorporated by reference herein in their entirety.

GOVERNMENT RIGHTS STATEMENT

The present invention was made with U.S. Government support under National Science Foundation (NSF) Grant No. CHE0649263. The U.S. Government has certain rights in the invention.

FIELD OF THE INVENTION

The present invention relates to polymeric materials including a glycosaminoglycan networked with a polyolefin-containing polymer. The present invention also relates to hydrogels containing the polymeric materials. The present invention further relates to methods of synthesizing the polymeric materials and hydrogels of the present invention.

BACKGROUND OF THE INVENTION

Hyaluronan (HA) is a ubiquitous, highly conserved macromolecule found in numerous species and present in almost every tissue in the body. HA has a long-standing history of use in numerous commercial applications including cosmetics, wound repair, drug delivery, and select biomedical engineering applications (e.g., cell-seeded hydrogels and scaffolds, osteochondral defect repairs). While its biocompatibility and bioactive properties make it an attractive biomaterial, its mechanical properties are insufficient for load-bearing applications. Attempts to improve mechanical properties have included various crosslinking methodologies, but commercially-available crosslinked HA hydrogels are still orders of magnitude weaker than required for many load-bearing biomedical applications. Therefore, there is a need for hydrogels that have suitable mechanical, biocompatibility, and bioactive properties.

The present invention is directed to overcoming these and other deficiencies in the art.

SUMMARY OF THE INVENTION

In one aspect, the present invention relates to a polymeric material including a glycosaminoglycan ("GAG") networked with a polyolefin-containing polymer. In one embodiment, the glycosaminoglycan networked with a polyolefin-containing polymer is synthesized by reacting a glycosaminoglycan constituent with a polyolefin constituent, where the glycosaminoglycan constituent includes a modified glycosaminoglycan, and where the polyolefin constituent includes an alternating copolymer of a polyolefin with an acid anhydride. Therefore, the polymeric material of the present invention includes a glycosaminoglycan covalently bound to a polyolefin-containing polymer.

In another aspect, the present invention relates to a method of synthesizing a polymeric material including a glycosaminoglycan networked with a polyolefin-containing polymer. This method involves reacting a glycosaminoglycan constituent with a polyolefin constituent under conditions effective to yield the polymeric material including a glycosaminoglycan networked with a polyolefin-containing polymer. The glycosaminoglycan constituent used in this method can be one or more modified glycosaminoglycans. The polyolefin constituent used in this method can be an alternating copolymer of a polyolefin with an acid anhydride. This method is effective to yield a polymeric material including a glycosaminoglycan networked with a polyolefin-containing polymer, where the glycosaminoglycan is covalently bound to the polyolefin-containing polymer. In a particular embodiment, the polymeric material synthesized by this method includes hyaluronan and poly(ethylene-alt-maleic anhydride) ("PEMA") covalently bound to one another.

In another aspect, the present invention relates to a polymeric material that includes a tripolymer glycosaminoglycan-polyolefin network, where the tripolymer glycosaminoglycan-polyolefin network is synthesized by reacting a first constituent, a second constituent, and a third constituent with one another, thereby yielding the tripolymer glycosaminoglycan-polyolefin network. The first constituent used to synthesize the tripolymer glycosaminoglycan-polyolefin network can include one or more modified glycosaminoglycans. The second constituent used to synthesize the tripolymer glycosaminoglycan-polyolefin network is an alternating copolymer of a polyolefin with an acid anhydride. The third constituent used to synthesize the tripolymer glycosaminoglycan-polyolefin network is a graft copolymer having a polyolefin backbone functionalized/grafted with an acid anhydride. The first constituent, the second constituent, and the third constituent react to form covalent bonds in the polymeric material.

In another aspect, the present invention relates to a method of synthesizing a polymeric material that includes a tripolymer glycosaminoglycan-polyolefin network. This method involves providing the following constituents: (i) a first constituent including one or more modified glycosaminoglycans; (ii) a second constituent including an alternating copolymer of a polyolefin with an acid anhydride; and (iii) a third constituent including a graft copolymer having a polyolefin backbone functionalized/grafted with an acid anhydride. The first constituent, the second constituent, and the third constituent are reacted under conditions effective to yield a tripolymer glycosaminoglycan-polyolefin network. The first constituent, the second constituent, and the third constituent react to form covalent bonds in the polymeric material. Suitable first, second, and third constituents for use in this method can include, without limitation, those as described herein above.

In another aspect, the present invention relates to a polymeric material including a glycosaminoglycan networked with a polyolefin-containing polymer, where the glycosaminoglycan networked with a polyolefin-containing polymer includes glycosaminoglycan covalently bound to a polyolefin-containing polymer. In a particular embodiment, the glycosaminoglycan is hyaluranon and the polyolefin-containing polymer is PEMA.

In another aspect, the present invention relates to hydrogels that include the polymeric materials of the present invention.

Hydrogels of the polymeric materials (including, for example, copolymers and tripolymers) of the present invention can be used for various purposes. For example, the hydrogels of the present invention can be used for orthopedic and other medical applications, including, without limitation, the following: (1) intervertebral disc repair, reconstruction, and regeneration; (2) cartilage repair, reconstruction, and regeneration; (3) meniscus repair, reconstruction, and regeneration; (4) soft tissue augmentation, repair, reconstruction, regeneration. Other possible uses and applications for the hydrogels of the present invention can include, without limitation, adhesion barriers; drug delivery vehicles; contact lenses; plant-florist shop flower gels; cooling bands, cooling mats, temperature and hydration control/regulation where biocompatibility is important; diapers; fire suppression; plastic surgery (e.g., facial augmentation, wrinkle injections, cosmetics, breast implants/augmentation); and water absorbing applications (e.g., super water absorbency).

The GAG-based hydrogels of the present invention are capable of absorbing many times their dry weight in water or saline and still maintain their mechanical integrity with swelling and have mechanical properties amenable to use in orthopedic implants (e.g., cartilage repair, meniscal repair, IVD repair). The GAG (e.g., HA) should make the hydrogel biocompatible and bioactive. Crosslinking the copolymer after synthesis improves network characteristics (e.g., mechanical integrity) and exhibits slightly decreased water absorption (swelling).

Reference is made to International Application No. PCT/US2008/005054, filed Apr. 18, 2008, which published as WO 2008/130647 on Oct. 30, 2008, and which claims benefit of priority to U.S. Provisional Patent Application Ser. No. 60/925,452, filed Apr. 19, 2007, the entire disclosures of which are hereby incorporated by reference in their entirety. The present application has at least one inventor in common with PCT/US2008/005054. The polymeric materials (including copolymers and tripolymers) of the present invention are distinct from the graft copolymer described in PCT/US2008/005054, but have some general similarities. For example, certain of the polymeric materials (including copolymers and tripolymers) of the present invention and the copolymers of PCT/US2008/005054 are similar in that they have —OH groups on GAG that react with maleic anhydride (MAH or MA) on maleated polyethylene (PE).

However, the polymeric materials (including copolymers and tripolymers) of the present invention are distinguishable from the copolymers of PCT/US2008/005054 in a number of important ways. For example, the polymeric materials (including copolymers and tripolymers) of the present invention are effective in producing hydrophilic hydrogels (i.e., a crosslinked network that maintains shape and mechanical integrity when swollen in aqueous solvents like water and absorbs many times its own weight in water). By way of contrast, the polymeric material made of the copolymer of PCT/US2008/005054 is an amphiphilic material.

Another distinction between the polymeric materials (including copolymers and tripolymers) of the present invention and the copolymers of PCT/US2008/005054 is with regard to the starting reactant. The copolymers of PCT/US2008/005054 used grafted MAH-PE as the starting reactant. By way of contrast, the polymeric materials (including copolymers and tripolymers) of the present invention uses an alternating MAH-PE (PEMA) copolymer as a starting reactant. Therefore, unlike the copolymer of PCT/US2008/005054, the reactive MAH groups of the polymeric materials (including copolymers and tripolymers) of the present invention are in the PE backbone (not grafted). In addition, compared to the copolymers of PCT/US2008/005054, the polymeric materials (including copolymers and tripolymers) of the present invention have significantly more MAH groups available for reaction.

Another distinction between the polymeric materials (including copolymers and tripolymers) of the present invention and the copolymers of PCT/US2008/005054 relates to the copolymerization reaction. Synthesis of the copolymers of PCT/US2008/005054 required a 2-phase reaction or emulsion reaction. By way of contrast, the polymeric materials (including copolymers and tripolymers) of the present invention only require a copolymerization reaction done in a single phase (e.g., DMSO). In one embodiment, the tripolymers of the present invention are synthesized using copolymers of both the present invention and of PCT/US2008/005054, except that 1,2,4-trichlorobenzene (TCB) is used in place of xylenes. DMSO is miscible with benzene but immiscible with xylene.

Another distinction between the polymeric materials (including copolymers and tripolymers) of the present invention and the copolymers of PCT/US2008/005054 relates to hydrogel characteristics. For example, the hydrogels made from the polymeric materials (including copolymers and tripolymers) of the present invention form an infinite network and are more gel-like than the copolymers of PCT/US2008/005054. In addition, in some cases the hydrogels of the present invention have physical crosslinks that do not last and more permanent chemical crosslinks with subsequent HMDI crosslinking.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

properties appropriate for NP in a physiological frequency range can be achieved via particulate reinforcement of the gel.

Figure 5:
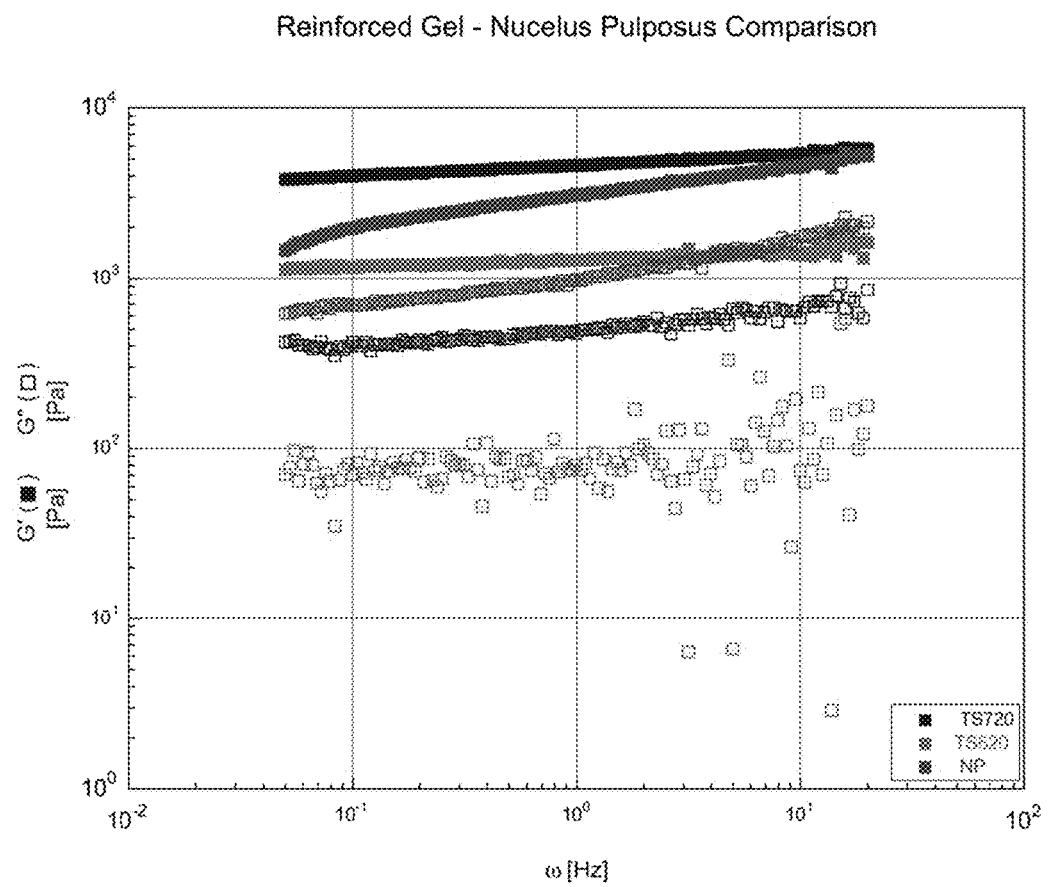

FIG. 5 is a graph showing representative storage (G') and loss (G") shear moduli for silica-reinforced 95:5 CoPEMA gels (TS-620 and TS-720) and ovine nucleus pulposus (NP) over the frequency range 0.05 Hz<f<20 Hz.

Figure 6:
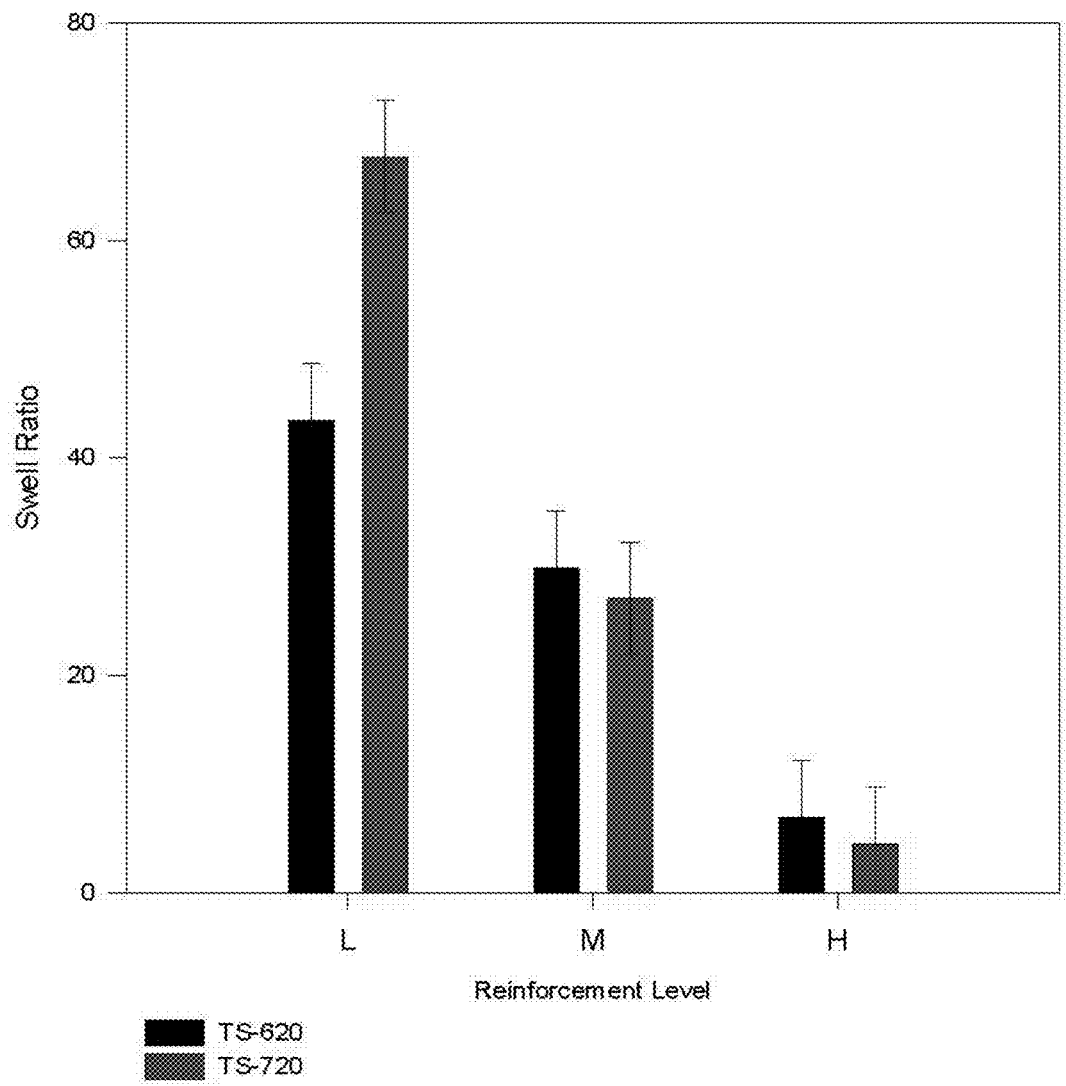

FIG. 6 is a graph showing the effect of reinforcement level with swell ratio of silica-reinforced 95:5 CoPEMA gels (TS-620 and TS-720). As silica content increases swell ratio decreases.

Figure 7:
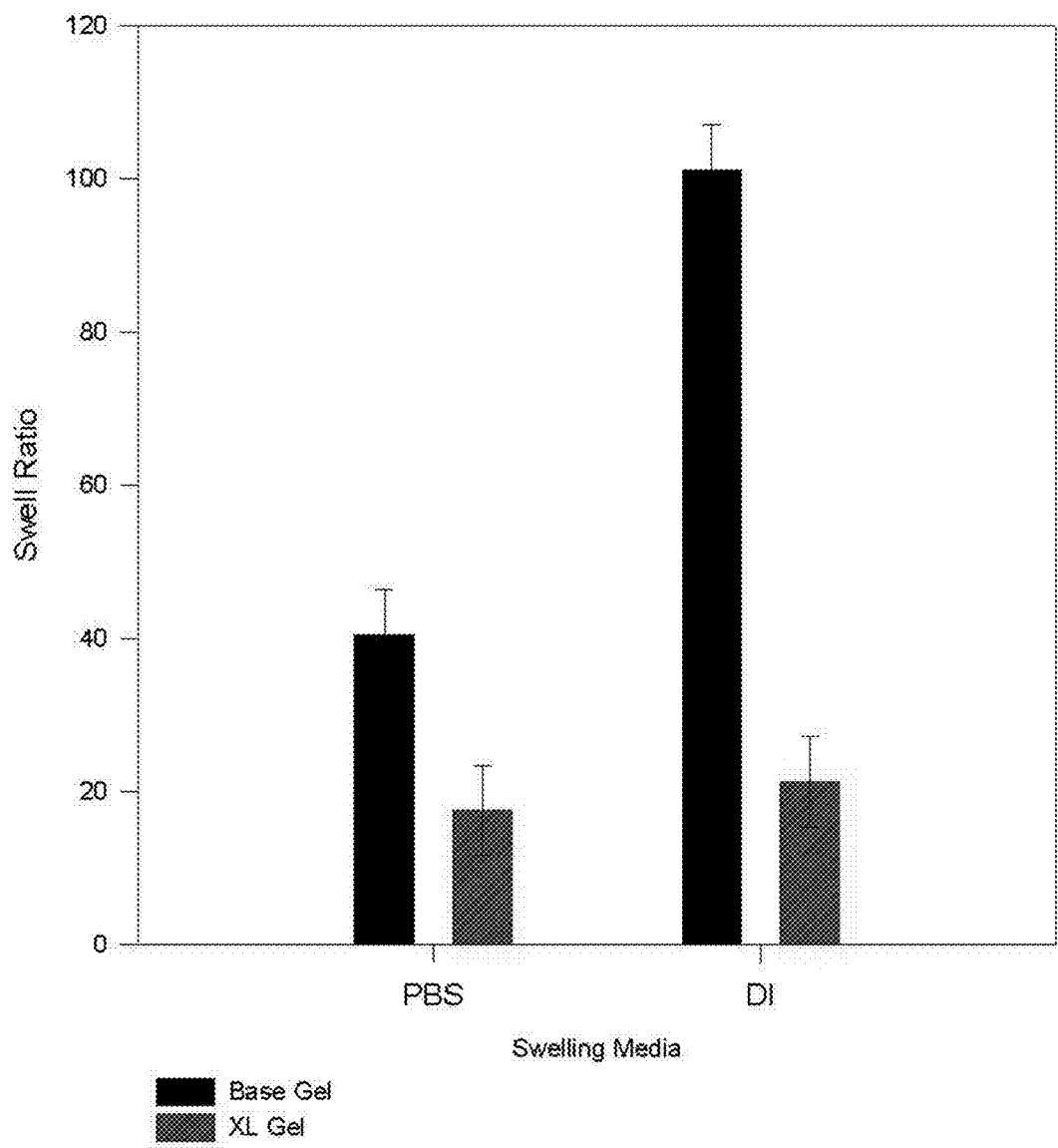

FIG. 7 is a graph showing the effect of crosslinking and solution on swell ratio. Swell ratio for untreated gels significantly increases in deionized water vs. phosphate buffered saline due to repulsive forces among negatively-charged hyaluronan molecules; charges are masked by cations in the PBS. No difference is seen in crosslinked gels.

Figure 8:
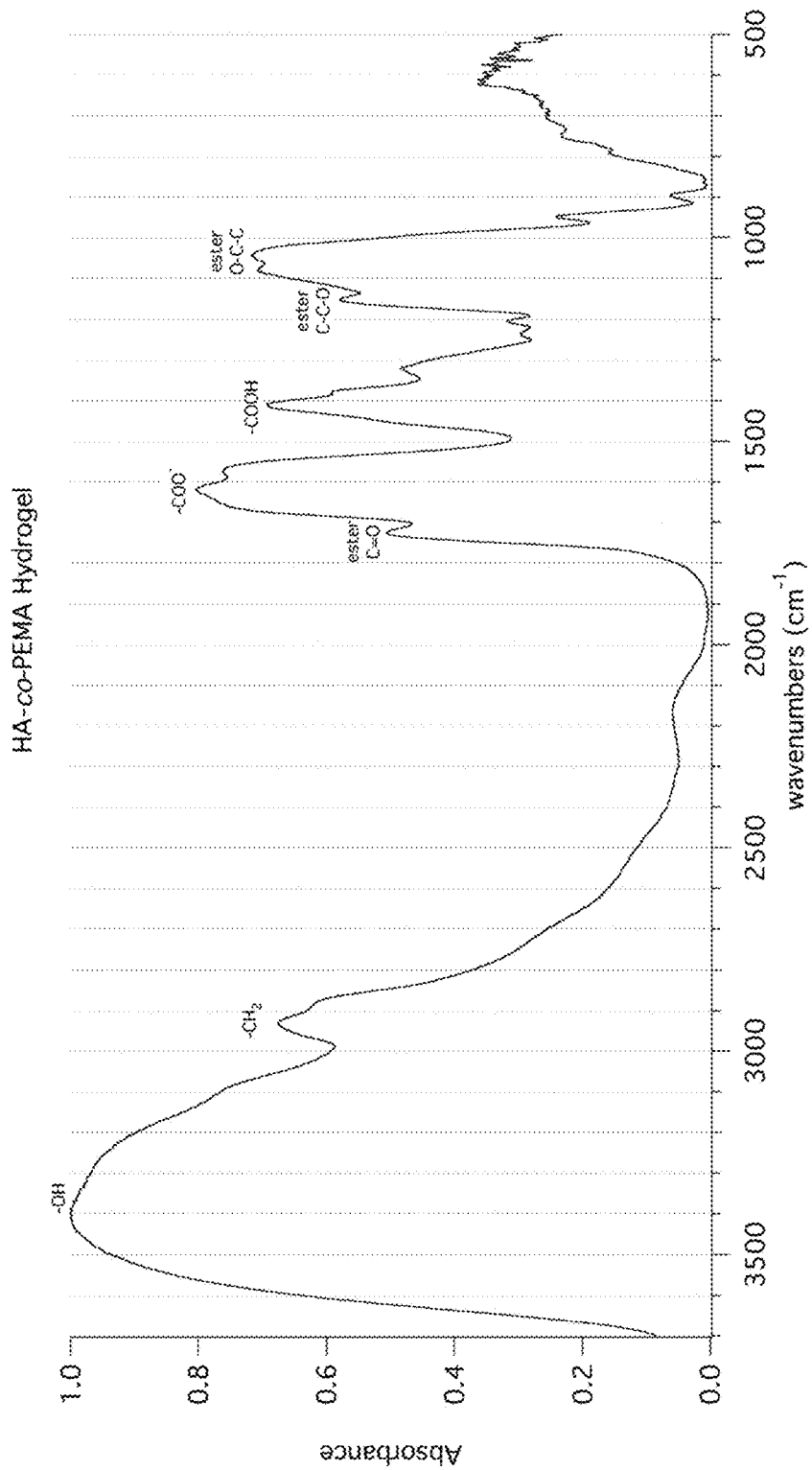

FIG. 8 is a graph showing an FTIR spectrum identifying 95:5 CoPEMA gel.

Figure 9:
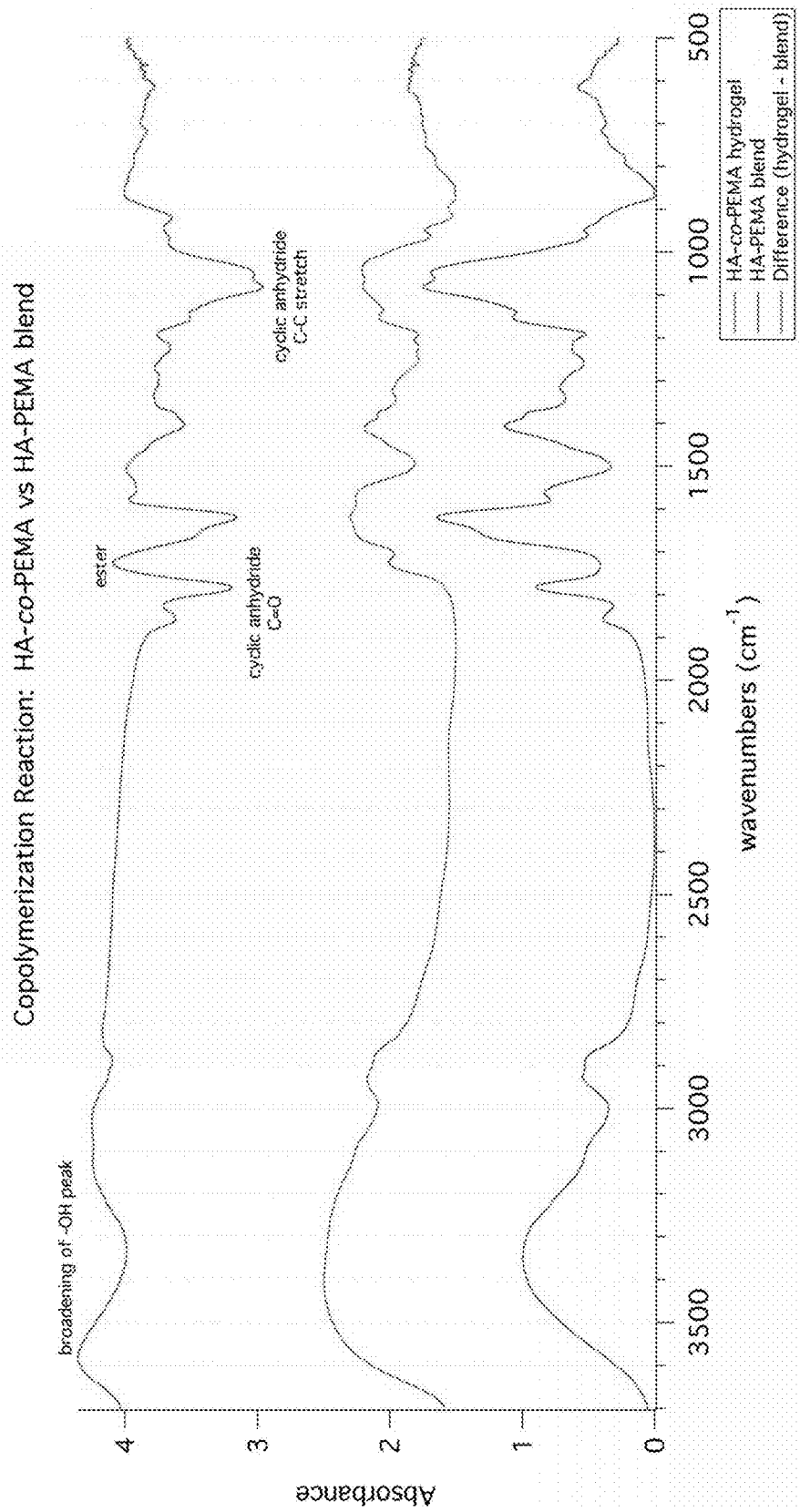

FIG. 9 is a graph showing FTIR spectra for CoPEMA gel vs. a control blend of HA and PEMA. The difference spectra (subtraction of control blend spectra from CoPEMA spectra) shows the development of an ester peak along with a decrease in anhydride moieties.

Figure 10:
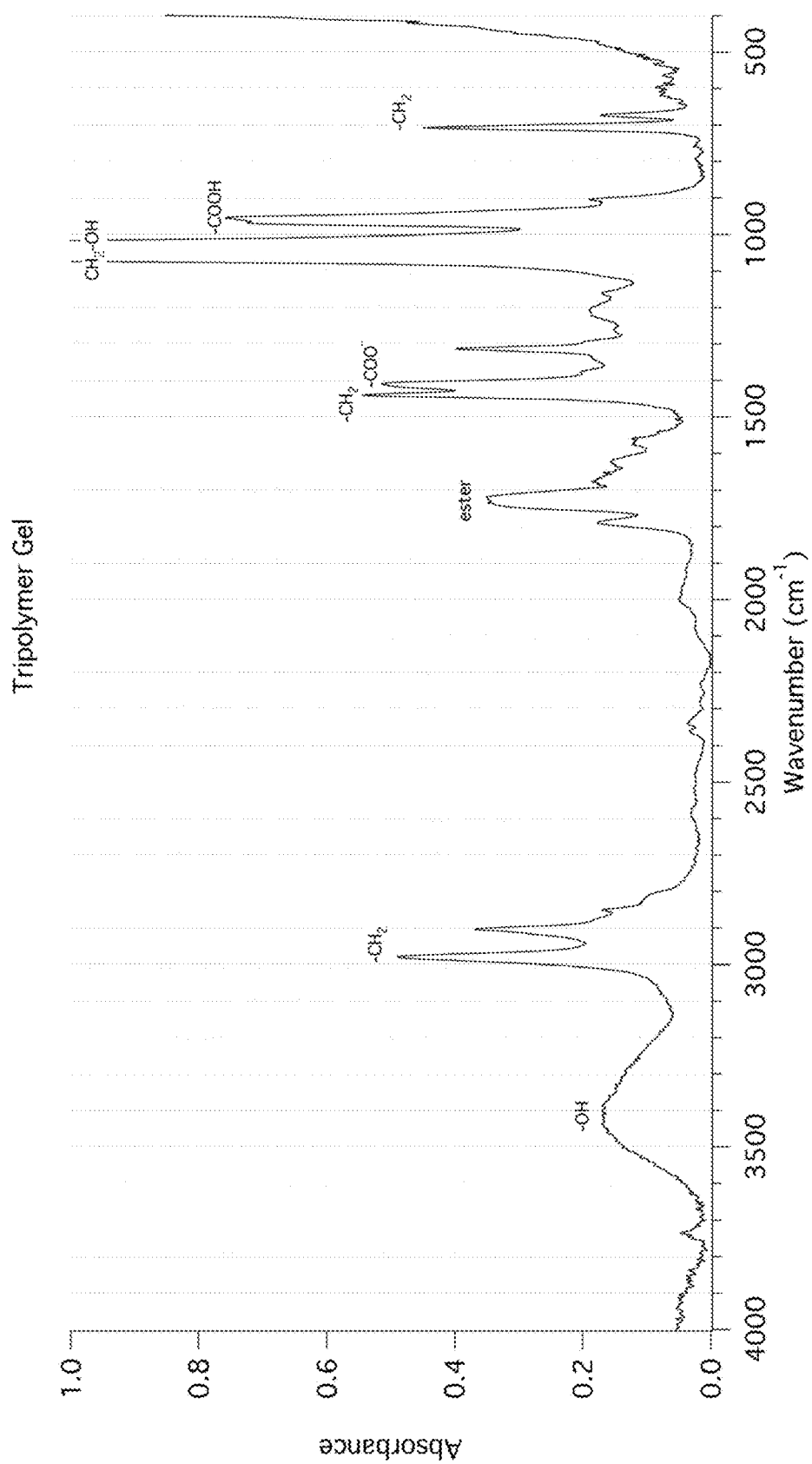

FIG. 10 is a graph showing an FTIR spectrum identifying 85:15:15 tripoly gel.

DETAILED DESCRIPTION OF THE INVENTION

The present invention generally relates to a polymeric material that includes a glycosaminoglycan networked with a polyolefin-containing polymer having a glycosaminoglycan covalently bound to a polyolefin-containing polymer. As described in more detail herein, one aspect of the present invention relates to an embodiment of the polymeric material that is synthesized from the combination of a modified glycosaminoglycan with an alternating copolymer of a polyolefin with an acid anhydride. The polymeric material of the present invention can be used in numerous applications, including, for example, in the preparation of hydrogels for use in medical devices.

Prior to discussing the present invention in detail, provided below are definitions of certain terms used to describe the present invention or aspects thereof. In general, the terms are used within their accepted meanings. The definitions provided herein below are meant to clarify, but not limit, the terms defined. Throughout this specification, the terms and substituents retain their definitions, unless otherwise stated.

A "polymer" is a substance composed of macromolecules, the structure of which essentially comprises the multiple repetition of units derived from molecules of low relative molecular mass.

A "monomer" that is polymerized along with one or more other monomers creates a "copolymer."

A "polyolefin" (also referred to in the relevant art as a "polyalkene") is a polymer produced from olefin, or alkene, as the monomer. For example, "polyethylene" is the polyolefin produced by polymerizing the olefin, ethylene. Polyethylene is a well-accepted engineering plastic with high toughness and good load bearing properties. Introducing polyethylene into HA hydrogels allows for improved mechanical integrity while retaining the hydrophilicity and bioactivity of HA. The mechanical properties can be tuned by varying constituent ratios and/or chemically crosslinking gels produced via the reactions described herein. "Polypropylene" is the name given to the polyolefin which is made from propylene.

"Synthetic polymers" encompass a large number of polymers, including, for example, polyethylene, polypropylene, polystyrene (a polymer made from the monomer styrene), etc.

A "copolymer" is a polymer derived from a mixture of two or more starting compounds, or monomers; a copolymer exists in many forms in which the monomers are arranged to form different types, or structures. The properties of a polymer depends both on the type of monomers that make up the molecule, and how those monomers are arranged. For example, a linear chain polymer may be soluble or insoluble in water depending on whether it is composed of polar monomers or nonpolar monomers, and also on the ratio of the former to the latter.

As used herein, a "tripolymer" is a polymer derived from a mixture of three or more starting compounds, monomers, polymers, or copolymers.

A "graft copolymer" can be synthesized by grafting one polymer onto a second polymer (i.e., rather than starting with monomers, synthesis starts with pre-polymerized polymers that are then grafted together). As used herein, graft copolymers can be identified by using the letter "g" or the word "graft" between the different polymers of a particular graft copolymer (e.g., polyethylene-graft-maleic anhydride).

An "alternating copolymer" refers to a copolymer having alternating monomers, as opposed to one polymer making up the backbone and the other polymer being grafted onto the backbone. As used herein, alternating copolymers can be identified by using the abbreviation "alt" or the word "alternating" between the different polymers of a particular alternating copolymer (e.g., poly(ethylene-alt-maleic anhydride)).

The terminology that has developed to describe polymers refers to both the nature of the monomers as well as their relative arrangement within the polymer structure. The most simple form of polymer molecule is a "linear" or "straight chain" polymer, composed of a single, linear backbone with pendant groups.

A "branched polymer molecule" is composed of a main chain, or "backbone," with one or more constituent side chains or branches (for example, branched polymers include star polymers, comb polymers, and brush polymers). If the polymer contains a side chain that has a different composition or configuration than the main chain, the polymer is considered a "graft" or "grafted polymer." Anhydride graft polyethylene is an example of a polyolefin that has been grafted with anhydride functional groups.

A "crosslink" suggests a branch point from which one polymer chain is covalently bound to another polymer chain, or a part of itself. A polymer molecule with a high degree of crosslinking is often referred to as a "polymer network" or an "elastomer." If there is a very high graft rate of a smaller (side chain) polymer molecule onto a larger (backbone) polymer molecule and there is a high graft rate and one side chain is grafted to more than one backbone molecule at a time, then the graft copolymer can form a polymer network.

As used herein, the terms "network" or "networked" or "polymer network" are used to describe a polymeric material in which the polymeric molecules are covalently bound to each other, resulting in a gel which will swell in a good solvent for the constituent polymers, but will not dissolve.

As used herein, the term "hydrogel" is meant to include a networked polymeric material in an aqueous solvent.

"Melt-processable" refers to those thermoplastic polymers that have a distinct thermodynamic, first order phase transition melting point that is below the degradation point of the polymer. Such a polymer will melt when heated, making it easier to form into different shapes, and when cooled down will recrystallize. Only the crystalline portion of the material actually melts, the amorphous regions do not. For most thermoplastic polymers, melting of the crystalline regions will make the polymer flow and thus make it thermally formable, if the melting point is well below the degradation point of the material.

"Glycosaminoglycan" (abbreviated as "GAG"), as used herein, is intended to include, without limitation, hyaluronan, chondroitin sulfate, dermatan sulfate, keratan sulfate, heparan sulfate, and heparin; these are generally considered to be biodegradable molecules.

A glycosaminoglycan is composed of a repeating disaccharide; that is, it has the structure -A-B-A-B-A-, where A and B represent two different sugars.

As used herein, "poly(ethylene-alt-maleic anhydride)" (abbreviated as "PEMA") is an alternating copolymer of polyethylene with maleic anhydride. Because PEMA is water-soluble, a polymeric material containing PEMA can be distinguished from other polymeric materials not containing PEMA (e.g., HA-g-HDPE) with higher swelling ratios and lower elastic/shear modulus. Using Fourier transform infrared (FTIR) spectroscopy, the polyolefin peaks are broader and less distinct.

PEMA can be described structurally as follows:

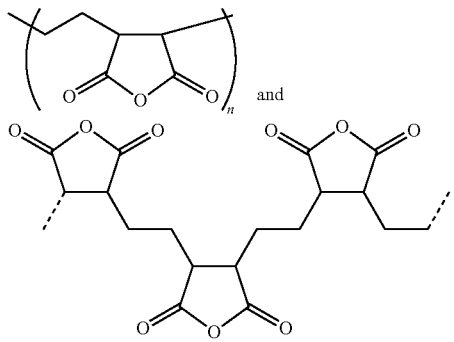

Poly(Ethylene-Alt-Maleic Anhydride) (PEMA)

In one aspect, the present invention relates to a polymeric material including a glycosaminoglycan networked with a polyolefin-containing polymer. In one embodiment, the glycosaminoglycan networked with a polyolefin-containing polymer is synthesized by reacting a glycosaminoglycan constituent with a polyolefin constituent, where the glycosaminoglycan constituent includes one or more modified glycosaminoglycans, and where the polyolefin constituent includes an alternating copolymer of a polyolefin with an acid anhydride. Therefore, the polymeric material of the present invention includes a glycosaminoglycan networked with a polyolefin-containing polymer where the glycosaminoglycan is covalently bound to a polyolefin-containing polymer.

As used herein, suitable glycosaminoglycans can include, without limitation, hyaluronan, chondroitin sulfates, dermatan sulfates, keratan sulfates, heparan sulfates, and heparin. Further, more than one type of glycosaminoglycan or modified glycosaminoglycan may be used or contained in the polymeric materials of the present invention. The glycosaminoglycan constituent can be a glycosaminoglycan modified with a paraffin ammonium cation dissociated from a salt, including, without limitation, alkyltrimethylammonium chloride, alkylamine hydrochloride, alkylpyridinium chloride, alkyldimethylbenzyl ammonium chloride, alkyltrimethylammonium bromide, alkylamine hydrobromide, alkylpyridinium bromide, and alkyldimethylbenzyl ammonium bromide. In a particular embodiment, the alkyltrimethylammonium bromide can be cetyl alkyltrimethylammonium bromide (CTAB).

As used herein, a suitable polyolefin can included, without limitation, polyethylene.

As used herein, a suitable acid anhydride can include, without limitation, maleic anhydride.

As used herein, the term polyolefin-containing polymer can include a polymer having an alternating copolymer of an olefin with maleic anhydride (e.g., PEMA).

In one embodiment, the polyolefin constituent can be an alternating copolymer of polyethylene with maleic anhydride, including, for example, poly(ethylene-alt-maleic anhydride) (PEMA) as described herein.

In another embodiment, the polyolefin constituent can include, without limitation, poly(ethylene-alt-maleic anhydride), poly(styrene-alt-maleic anhydride), poly(isobutylene-alt-maleic anhydride), poly(maleic anhydride-alt-1-octadecene), poly(methyl vinyl ether-alt-maleic anhydride), and derivatives thereof.

In another embodiment, the polyolefin-containing polymer can include, without limitation, poly(ethylene-alt-maleic anhydride), poly(styrene-alt-maleic anhydride), poly(isobutylene-alt-maleic anhydride), poly(maleic anhydride-alt-1-octadecene), poly(methyl vinyl ether-alt-maleic anhydride), and derivatives thereof.

A structural representation of one embodiment of the polymeric material of the present invention (CoPEMA) is provided below:

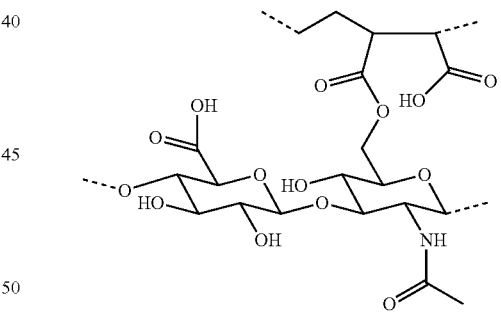

In another embodiment, the polymeric material can further include a reinforcing agent. The reinforcing agent can be an inorganic reinforcing agent, an organic reinforcing agent, or a mixture thereof. Suitable examples of inorganic reinforcing agents can include, without limitation, inorganic agents such as silica, alumina, zirconia, calcium phosphates, and hydroxyapatite, as well as compositions containing these inorganic agents. Suitable examples of organic reinforcing agents can include, without limitation, carbon nanotubes, carbon nanofibers, chitosan nanofibers, demineralized bone matrix (DBM), collagen, silk, and cellulose. Further, the inorganic reinforcing agents and the organic reinforcing agents can be modified to provide additional desired characteristics to the polymeric material. For example, the reinforcing agent can be surface-modified. In one embodiment, the inorganic reinforcing agent can be silica modified with polydimethylsiloxane to make it hydrophobic. Suitable reinforcing agents can also include synthetic polymers well known in the art and readily available. For example, suitable synthetic polymers for use as reinforcing agents can include, without limitation, DACRON®, TEFLON®, KEVLAR®, and the like. Other reinforcing agents can include, without limitation, any non-water soluble agent (e.g., fiber, particulate) that provides reinforcement to the polymeric material, and that does not interfere with synthesis of the polymeric material. One of ordinary skill in the art can readily determine various reinforcing agents suitable for use in the present invention, as well as suitable modifications to the reinforcing agents.

The present invention also relates to a method of synthesizing a polymeric material including a glycosaminoglycan networked with a polyolefin-containing polymer. This method involves reacting a glycosaminoglycan constituent with a polyolefin constituent under conditions effective to yield the polymeric material including a glycosaminoglycan networked with a polyolefin-containing polymer. The glycosaminoglycan constituent used in this method can be one or more modified glycosaminoglycans. The polyolefin constituent used in this method can be an alternating copolymer of a polyolefin with an acid anhydride. This method is effective to yield a polymeric material including a glycosaminoglycan networked with a polyolefin-containing polymer, where the glycosaminoglycan is covalently bound to the polyolefin-containing polymer. In a particular embodiment, the polymeric material synthesized by this method includes hyaluronan and PEMA covalently bound to one another.

In one embodiment, the reacting step of the above method of synthesizing the polymeric material is an esterification reaction between the glycosaminoglycan constituent and the polyolefin constituent. The various glycosaminoglycan constituents and polyolefin constituents suitable for use in this method are as described herein.

Set forth for illustration purposes is a synthetic scheme (Scheme 1) that generally depicts one embodiment of the synthesis of the polymeric material of the present invention, as follows:

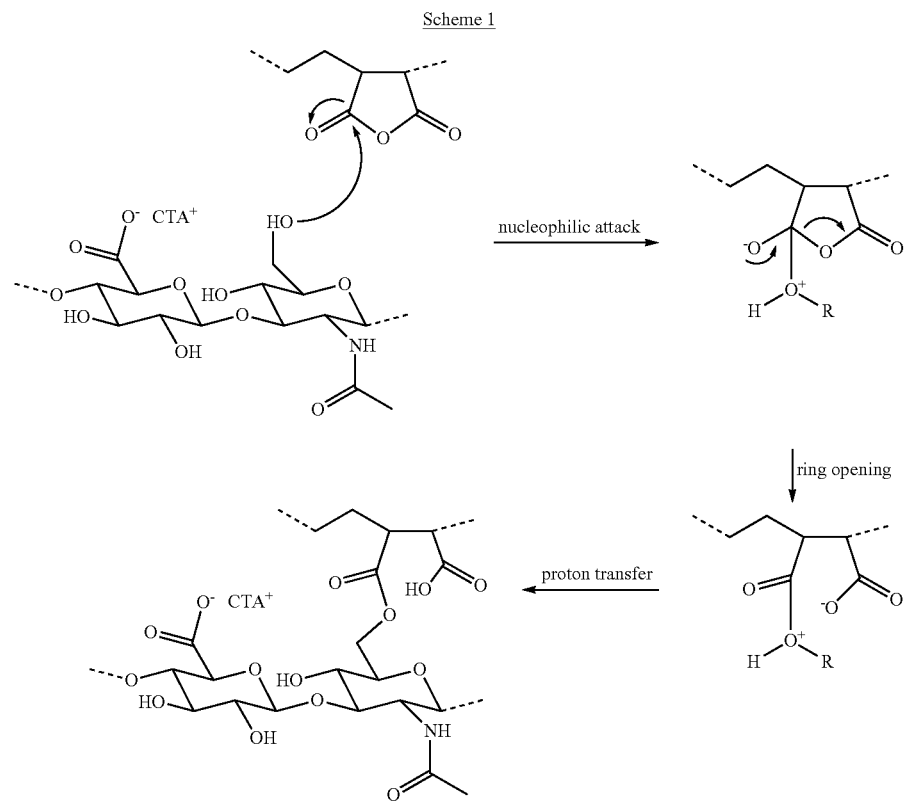

Scheme 1

In view of Scheme 1, one of ordinary skill in the art can see that in the final hydrolyzed form, the glycosaminoglycan (i.e., hyaluronan (HA)) is no longer a "modified" glycosaminoglycan as it is when the reaction is occurring. As shown in this scheme, the modified glycosaminoglycan can be HA-CTA (HA complexed with cetyltrimethyl ammonium salt). Further, the polyolefin-containing polymer (i.e., PEMA) maintains the PE-alt-MA structure, but the MA (maleic anhydride) ring has opened up and reacted (bonded) to the HA, or has remained open in acid form.

In another embodiment, the above method of synthesizing the polymeric material can further include incubating the glycosaminoglycan constituent and the polyolefin constituent in a crosslinker constituent. Suitable crosslinker constituents can include any molecule or composition that is effective to crosslink with an alcohol group of the glycosaminoglycan constituent. For example, suitable crosslinker constituents can include, without limitation, diisocyanates, polyisocyanates, hexamethylenediisocyanate (HMDI), methylene diphenyl diisocyanate, toluene diisocyanate, isophorone diisocyanate, divinyl sulphone, poly (ethylene glycol) diglycidyl ether, phosphoryl chloride, glutaraldehyde, dialdehyde via Passerini reaction, diamine via Ugi reaction, and carbodiimide.

In another embodiment, the above method of synthesizing the polymeric material can further include combining the glycosaminoglycan constituent and the polyolefin constituent with a reinforcing agent. Suitable reinforcing agents are as described herein. In view of the present specification and the teachings in the relevant art, one of ordinary skill would readily discern the types of reinforcing agents that can be used in the present invention, as well as the concentrations and protocols.

The present invention further relates to a polymeric material that includes a tripolymer glycosaminoglycan-polyolefin network, where the tripolymer glycosaminoglycan-polyolefin network is synthesized by reacting a first constituent, a second constituent, and a third constituent with one another, thereby yielding the tripolymer glycosaminoglycan-polyolefin network. The first constituent used to synthesize the tripolymer glycosaminoglycan-polyolefin network can include one or more a modified glycosaminoglycans. The second constituent used to synthesize the tripolymer glycosaminoglycan-polyolefin network is an alternating copolymer of a polyolefin with an acid anhydride. The third constituent used to synthesize the tripolymer glycosaminoglycan-polyolefin network is a graft copolymer having a polyolefin backbone functionalized/grafted with an acid anhydride. The first constituent, the second constituent, and the third constituent react to form covalent bonds in the polymeric material.

Suitable first and second constituents of the tripolymer glycosaminoglycan-polyolefin network are those as described herein above as the modified glycosaminglycan and the alternating copolymer of a polyolefin with an acid anhydride. Further, a suitable third constituent of this tripolymer glycosaminoglycan-polyolefin network can include, without limitation, maleic anhydride-graft-polyethylene, maleic anhydride-graft-polypropylene, maleic anhydride-graft-polystyrene, polystyrene-graft-maleic anhydride, polyisoprene-graft-maleic anhydride, and polypropylene-graft-maleic anhydride.

In one embodiment, the tripolymer glycosaminoglycan-polyolefin network includes hyaluron as the first constituent, poly(ethylene-alt-maleic anhydride) as the second constituent, and maleic anhydride-graft-polyethylene as the third constituent.

Structural representations of poly(ethylene-alt-maleic anhydride) (also referred to as PE-alt-MA and PEMA) is provided above.

Structural representations of a maleic anhydride-graft-polyethylene (also referred to as PE-g-MA) is provided below:

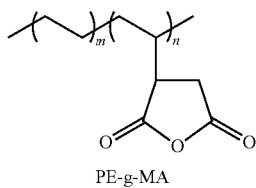

PE-g-MA

In another embodiment, the tripolymer glycosaminoglycan-polyolefin network can further include a reinforcing agent as described herein, a crosslinker constituent as described herein, or both.

In some embodiments, the polymeric material according to the invention or the hydrogel according to the invention is non-biodegradable or is resistant to biodegradation.

In this way, such embodiments differ from, e.g., the materials disclosed in U.S. Pat. No. 6,833,488 B2, which is hereby incorporated by reference herein. In some embodiments, the polymeric material or hydrogel of the invention are not capable of being decomposed by bacteria or other living organisms. In some embodiments, the polymeric material or hydrogel of the invention are not capable of being decomposed by bacteria or other living organisms over a predefined period (e.g., a period of at least 5 to at least 365 days (e.g., at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, or 365 days)).

The present invention also relates to a method of synthesizing a polymeric material that includes a tripolymer glycosaminoglycan-polyolefin network. This method involves providing the following constituents: (i) a first constituent including one or more modified glycosaminoglycans; (ii) a second constituent including an alternating copolymer of a polyolefin with an acid anhydride; and (iii) a third constituent including a graft copolymer having a polyolefin backbone functionalized/grafted with an acid anhydride. The first constituent, the second constituent, and the third constituent are reacted under conditions effective to yield a tripolymer glycosaminoglycan-polyolefin network. The first constituent, the second constituent, and the third constituent react to form covalent bonds in the polymeric material. Suitable first, second, and third constituents for use in this method can include, without limitation, those as described herein above.

In one embodiment, the reacting step of the above method of synthesizing the polymeric material (i.e., that includes a tripolymer glycosaminoglycan-polyolefin network) is an esterification reaction between the first constituent and the second and third constituents. The various constituents suitable for use in this method are as described herein.

In another embodiment, the above method of synthesizing the polymeric material (i.e., that includes a tripolymer glycosaminoglycan-polyolefin network) can further include incubating the first, second, and third constituents in a crosslinker constituent. Suitable crosslinker constituents are as described herein.

In another embodiment, the above method of synthesizing the polymeric material (i.e., that includes a tripolymer glycosaminoglycan-polyolefin network) can further include combining the first, second, and third constituents with a reinforcing agent. Suitable reinforcing agents are as described herein.

In another aspect, the present invention relates to a polymeric material including a glycosaminoglycan networked with a polyolefin-containing polymer, where the glycosaminoglycan networked with a polyolefin-containing polymer includes glycosaminoglycan covalently bound to a polyolefin-containing polymer. In a particular embodiment, the glycosaminoglycan is hyaluranon and the polyolefin-containing polymer is PEMA.

In another aspect, the present invention relates to hydrogels that include the polymeric materials of the present invention. One of ordinary skill, in view of the teachings provided herein, can readily determine how to prepare a hydrogel that includes a polymeric material of the present invention.

The polymeric materials and hydrogels of the present invention can be distinguished from other polymeric materials and hydrogels using various techniques well known in the art. For example, Fourier transform infrared (FTIR) spectroscopy can be used to determine covalent bonding in the polymeric material/hydrogel by analyzing the formation of ester bonds between the constituents. Swelling properties can also be analyzed, where certain embodiments of the polymeric materials/hydrogels of the present invention exhibit swelling, but not dissolving, in an aqueous medium. Additionally, mechanical properties of the polymeric materials/hydrogels of the present invention can be used to distinguish them from other polymeric materials and hydrogels.

Description of PCT/US2008/005054

As discussed herein above, the polymeric material, copolymers, and tripolymers of the present invention are distinguishable from the copolymers disclosed in International Application No. PCT/US2008/005054, filed Apr. 18, 2008, which published as WO 2008/130647 on Oct. 30, 2008, and which claims benefit of priority to U.S. Provisional Patent Application Ser. No. 60/925,452, filed Apr. 19, 2007. The present application shares at least one inventor in common with PCT/US2008/005054.

One embodiment of a particular copolymer of PCT/US2008/005054 involved glycosaminoglycan covalently bound to polyethylene-graft-maleic anhydride. The tripolymer of the present invention includes as one of three constituents the polyethylene-graft-maleic anhydride.

Therefore, included below are portions of the disclosure of PCT/US2008/005054, substantially as set forth in PCT/US2008/005054.

A. Abstract of PCT/US2008/005054

A new copolymer synthesized from a glycosaminoglycan (GAG) such as hyaluronan/hyaluronic acid (HA), chondroitin sulfates, dermatan sulfates, keratin sulfates, heparin sulfate, and heparin, and an anhydride functionalized hydrophobic polymer, i.e., any polyolefin which has been 'functionalized' (grafted onto the backbone or incorporated into the backbone) with anhydride functional groups, such as maleic anhydride-graft-polyethylene, (or, maleated polyethylene), maleic anhydride-graft-polystyrene, maleic anhydride-graft-polypropylene, etc. The functionalized polyolefin may be a polyolefin backbone to which the anhydride functional groups have been grafted, or otherwise incorporated with the backbone. Also, a unique synthesis technique combines a modified GAG with a graft polyolefin, resulting in a unique copolymer with its constituents by-and-large covalently bound to each other.

B. Technical Field of PCT/US2008/005054

In general, the invention relates to polymers and polymeric systems, as well as associated techniques for synthesizing polymers. More particularly, one aspect is directed to a new copolymer synthesized from a glycosaminoglycan (or simply, GAG) such as hyaluronan/hyaluronic acid (HA), chondroitin sulfates, dermatan sulfates, keratin sulfates, heparin sulfate, and heparin, and an anhydride functionalized hydrophobic polymer, i.e., any polyolefin which has been 'functionalized' (grafted onto the backbone or incorporated into the backbone) with anhydride functional groups, such as maleic anhydride-graft-polyethylene, (known, also, as maleated polyethylene), maleic anhydride-graft-polystyrene, maleic anhydride-graft-polypropylene, and so on. The unique synthesis technique also disclosed, to combine a modified GAG with a graft polyolefin, results in a unique copolymer with its constituents by-and-large covalently bound to each other. While GAG's such as hyaluronan, or hyaluronic acid, are generally non-melt-processable and biodegradable, hydrophobic polymers such as polyolefins to which anhydride functional groups have been grafted, e.g., maleic anhydride-graft-polyethylene/maleated polyethylene, are usually melt-processable and non-biodegradable.

Depending on the ratio and molecular weight of reactants (i.e., main constituents of copolymer), and graft percent of maleic anhydride onto the polyolefin, one aspect of the novel copolymer is an amphiphilic, biphasic construct consisting of a glycosaminoglycan (GAG) backbone and synthetic polymeric side chains; a second aspect comprises a synthetic polymer backbone with GAG side chains; and a third aspect comprises a continuous network of GAG and synthetic polymer, in which the synthetic polymer acts as crosslinks between different GAG chains or vice versa. The synthesis and characterization of the various identified aspects of the novel copolymer will be appreciated in connection with the technical discussion set forth, herein.

The anhydride functional groups grafted to the polyethylene chain are highly reactive compared to the hydrolyzed form of anhydrides, dicarboxylic acid. Hydrolysis occurs in the presence of water; for this reason, the reactions (details of which are included in the discussion identified as Example 1) were performed in an inert atmosphere (e.g. dry medical grade nitrogen gas) and in non-aqueous solvents. Hyaluronan/hyaluronic acid (HA) is immiscible with non-polar (i.e. nonaqueous) solvents. Here, the glycosaminoglycan was first modified with, by way of example, an ammonium salt to decrease the polarity of the molecule ("modified glycosaminoglycan"); such a uniquely modified glycosaminoglycan was miscible with non-polar solvents (e.g. dimethyl sulfoxide). Other modified GAG's are contemplated; for example, the GAG may be modified with other paraffin ammonium cations dissociated from a salt selected from the group consisting of alkyltrimethylammonium chloride, alkylamine hydrochloride, alkylpyridinium chloride, alkyldimethylbenzyl ammonium chloride, alkyltrimethylammonium bromide, alkylamine hydrobromide, alkylpyridinium bromide, and alkyldimethylbenzyl ammonium bromide.

The anhydride graft polyethylene is miscible with xylenes at 135° C. The novel amphiphilic copolymer was washed and the modified glycosaminoglycan portion of the copolymer was reverted back to its unmodified chemical structure through hydrolysis.

Applicant's Earlier Work in Synthesizing Hydrophobic-Hydrophilic Polymers.

The assignee hereof also owns U.S. Pat. No. 10,283,760 filed 29 Oct. 2002, James et al., entitled "Outer Layer having Entanglement of Hydrophobic Polymer Host and Hydrophilic Polymer Guest," Pub. No. US 2003/0083433 on 1 May 2003 describing earlier design and research efforts of at least one applicant-inventor hereof, and is fully incorporated herein by reference to the extent it provides supportive technological information of the unique copolymer, and its synthesis, and is consistent with this technical discussion. The assignee hereof also owns PCT International App. No. PCT/US2004/030666 filed 20 Sep. 2004, James et al., entitled "Hyaluronan (HA) Esterification via Acylation Technique for Moldable Devices," international pub. No. WO 2005/028632 A2 describing other earlier related research and development efforts of at least one applicant-inventor hereof.

C. Summary Disclosure of PCT/US2008/005054

One will appreciate the many distinguishable features of copolymer described herein from conventional products. Certain of the unique features of the invention, and further unique combinations of features—as supported and contemplated herein—provide a variety of advantages.

Briefly described, once again, the invention is directed to a novel copolymer synthesized from a glycosaminoglycan (e.g. hyaluronan, chondroitin sulfate, dermatan sulfate, keratan sulfate, heparan sulfate, heparin), and an anhydride functionalized hydrophobic polymer (such as any melt-processable polyolefin which has been grafted, or otherwise incorporated, with anhydride functional groups, e.g. anhydride graft polyethylene). The copolymer includes an amphiphilic, biphasic construct composed of a glycosaminoglycan (GAG) and a synthetic polymer. Also characterized is an associated novel process for synthesizing the copolymer.

One aspect of the invention is directed to a new copolymer synthesized from a glycosaminoglycan (GAG) such as hyaluronan, or hyaluronic acid (HA), chondroitin sulfates, dermatan sulfates, keratan sulfates, heparan sulfate, and heparin, and an anhydride functionalized hydrophobic polymer, i.e., any polyolefin which has been 'functionalized' (grafted onto the backbone or incorporated into the backbone) with anhydride functional groups; many such functionalized hydrophobic polymers are contemplated, such as maleic anhydride-graft-polyethylene (or simply, maleated polyethylene), maleic anhydride-graft-polystyrene, maleic anhydride-graft-polypropylene, and so on. The unique synthesis technique described herein to combine a modified GAG with an anhydride functionalized hydrophobic polymer, such as a graft poly olefin, results in a unique copolymer with its constituents by-and-large covalently bound to each other. One aspect of the novel copolymer is an amphiphilic, biphasic construct consisting of a glycosaminoglycan (GAG) backbone and synthetic polymeric side chains; a second aspect comprises a synthetic polymer backbone with GAG side chains; and a third aspect comprises a continuous network of GAG and synthetic polymer.

D. Description Detailing Features of PCT/US2008/005054

By viewing the figures depicting representative embodiments—further details included and labeled Example 1—of the unique copolymer and process to synthesize same, one can further appreciate the unique nature of core as well as additional and alternative features that are within the spirit and scope of this technical discussion. Reference has been made to various features—those depicted in the figures and diagrams (including those incorporated within an Example)—by way of back-and-forth reference and association.

Turning, first, to FIG. 6 of PCT/US2008/005054: the copolymer synthesis technique represented at 20 joins a modified glycosaminoglycan dissolved in non-aqueous solvent 22A, e.g., hyaluronan complexed with ammonium salt (HA-CTA), with an anhydride graft polyethylene also having been dissolved in a non-aqueous solvent 22B, e.g., maleic anhydride graft polyethylene (MA-g-HDPE). The anhydride functional groups grafted to the polyethylene chain are highly reactive compared to the hydrolyzed form of anhydrides, dicarboxylic acid. Since hydrolysis occurs in the presence of water, the copolymer reaction must be performed in an inert atmosphere (e.g. dry industrial nitrogen or argon gas) and in non-aqueous solvents; see, also FIG. 2 of PCT/US2008/005054. A covalent bond forms between the modified glycosaminoglycan and the anhydride graft polyethylene (24) forming the structure HA-CTA-co-HDPE (see, FIG. 7 of PCT/US2008/005054 at 30).

Once the copolymer reaction is complete, hydrolysis is purposely performed converting the modified glycosaminoglycan portion of the copolymer back to 'unmodified' glycosaminoglycan resulting in the GAG-poly olefin copolymer (in this specific example, HA-co-HDPE, box 26). Due to hyaluronan's immiscibility with non-polar (i.e. non-aqueous) solvents, the glycosaminoglycan was first modified with an ammonium salt to decrease the polarity of the molecule (i.e. modified glycosaminoglycan) 22A; once this was achieved the modified glycosaminoglycan was miscible with non-polar solvents (e.g. dimethyl sulfoxide). The anhydride graft polyethylene is miscible with xylenes at above approximately 100° C. As mentioned, the novel amphiphilic copolymer was washed and the modified glycosaminoglycan was reverted back to its unmodified chemical structure through hydrolysis (box 26, FIG. 6 of PCT/US2008/005054; see also FIG. 7 of PCT/US2008/005054). The glycosaminoglycan or polyolefin portions of the graft copolymer are now available for further processing (box 28), e.g, may be crosslinked. This may be performed 'individually' as is suggested at 28: crosslink HA portion with poly(diisocyanate) to form XLHA-g-HDPE; and crosslink HDPE portion with dicumyl peroxide.

A wide range of applications of the new copolymer are contemplated, to include a variety of devices and procedures, including but not limited to: total joint arthroplasty (as part or all of implant), hemi-arthroplasty, partial hemi-arthroplasty, scaffold for tissue engineering (specifically articular cartilage), meniscus replacement, catheters, condoms, cosmetics, wound dressing, ear tubes for chronic ear infections, carrier for drugs, demineralized bone matrix and bone morphogenetic proteins, bone defect filler, cosmetic surgery, maxio-facial reconstructions, non fouling coating for catheters, tissue engineering scaffold, anti adhesive film or coating, soft tissue augmentation—meniscus, cartilage, spinal disc, temporomandibular disc replacement, low friction coating on instruments/devices, wound covering (non-stick bandage, etc), viscosupplementation, eye surgery lubricant, etc.

EXAMPLES

The following examples are intended to illustrate particular embodiments of the present invention, but are by no means intended to limit the scope of the present invention.

Example 1

Synthesis of HA-CTA-Co-HDPE and its Hydrolysis to Yield HA-Co-HDPE

This example corresponds to Example 1 of PCT/US2008/005054 (discussed herein above). This example discusses the synthesis of HA-CTA-co-HDPE and its hydrolysis to yield HA-co-HDPE (reaction conditions given for 98 and 85% HA HA-CTA-co-HDPE with HA molecular weight of 1.5 MDa, and 0.3% MA (graft percent) MA-g-HDPE wherein the HDPE has a molecular weight of 121.5 kg/mol).

Complexation methods for sodium HA with CTAB are known. See, by way of further example: Zhang, M. and James, S. P.: Novel Hyaluronan Esters for Biomedical Applications, *Rocky Mountain Bioengineering Symposium, Biomedical Sciences Instrumentation* 238, 2004; Zhang, M. and James, S. P.: Silylation of hyaluronan to improve hydrophobicity and reactivity for improved processing and derivatization, Polymer 46:3639, 2005; and Zhang, M. and James, S. P.: Synthesis and properties of melt-processable hyaluronan esters, *Journal of Materials Science: Materials in Medicine* 16:587 (2005).

In U.S. Pat. No. 10,283,760, James et al., "Outer Layer having Entanglement of Hydrophobic Polymer Host and Hydrophilic Polymer Guest," U.S. Patent Application Publication No. US 2003/0083433 (mentioned above) on May 1, 2003, such complexes of HA were discussed:

Begin Quoted Text

Example 2

(1) Reaction of HA with long-chain aliphatic quaternan ammonium salts ($QN^+$). Polyanions, such as HA. combined with certain organic cations, such as paraffin chain ammonium ($QN^+$) ions, produces a precipitable complex. The complex is a true salt of the polyaad and quaternary base. HA was modified with long-chain aliphatic ammonium salts, to improve its solubility in organic solvents. Combination of QN+ with polyannions occurs in those pH ranges in which the polyannions are negatively charged. The reaction between HA and ammonium cations in water can be expressed:

$$HA^--Na^+ + QN^+A^- \rightarrow HA^--QN^+\downarrow + Na^+A^-$$

where $HA^--Na^+$ is the sodium salt of hyaluronic acid; $HA^{31}QN^+$ is the precipitable complex between HA carboxylic polyanion and long chain paraffin ammonium cations. $HA^-QN^+$ (HA-CPC/HA-CTAB) complexes were used. The complexes ($HA^-QN^+$) precipitated from HA aqueous solution are soluble in concentrated salt solutions, so HA can be recovered from its insoluble complexes. Ammonium salts used were: cetyltrimethylammonium bromide monohydrale (MW: 358.01) (CTAB) and cetylpyridinum chloride (M.W. 364.46) (CPC).

End Quoted Text

Briefly, for this Example 1, aqueous solutions of 0.2% (w/v) sodium HA and 1.0% (w/v) CTAB were mixed at room temperature to precipitate the HA-CTA. The precipitate was centrifuged, washed with $H_2O$ several times to remove $Na^+Br^-$ salt, and vacuum dried at room temperature for 72 hours (or until no change in weight was observed). The molecular weight of HA-CTA was determined to be $2.48 \times 10^6$ Da. HA-CTA and MA-g-HDPE, are the two constituents of the graft copolymer HA-co-HDPE, and their structures are shown below; however, the MA-g-HDPE used in this study was HDPE with MA grafted (0.36 weight %) randomly along the HDPE backbone, unlike the structure shown below (bottom chemical structure), where it appears such that the MA is grafted at the 'tail-end' of the HDPE chains:

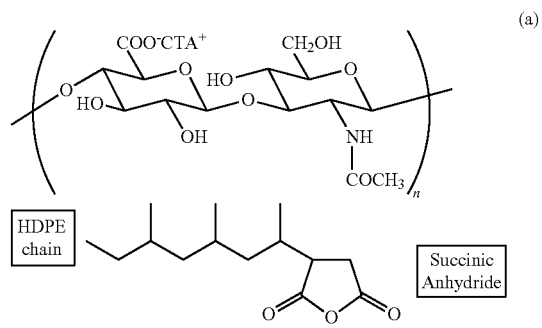

(a)

Chemical Structures: Top Structure is of HA-CTA; and Bottom is of MA-g-HDPE.

A 0.1% (w/v) solution of MA-g-HDPE in xylenes was refluxed for two hours at 135° C. under a dry $N_2$ atmosphere ensuring all of the MA-g-HDPE had gone into solution. HA-CTA was dissolved in DMSO at 80° C. (a 0.5% (w/v) solution). The MA-g-HDPE solution was added to the HA-CTA solution via a heated cannula (FIG. 2 of PCT/US2008/005054) under dry $N_2$ flow (see chemical structures diagrammed immediately below):

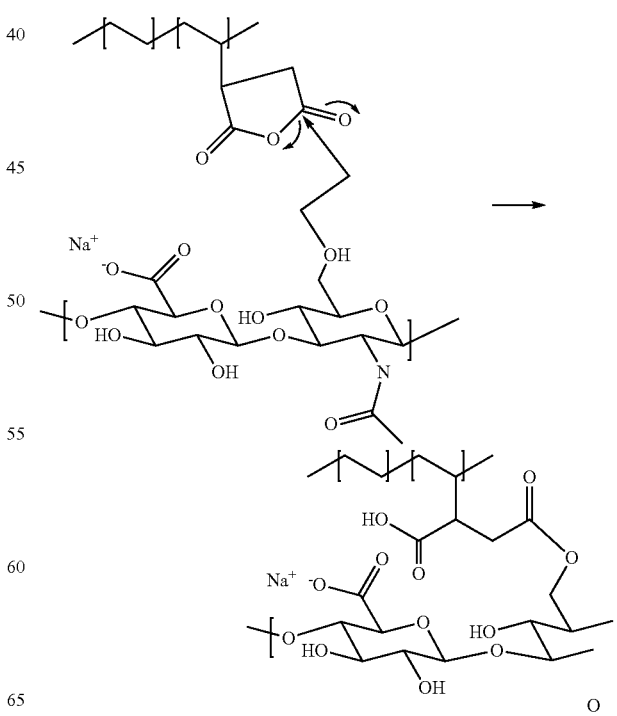

Chemical Structures of: (left-side) HA-CTA; and (right-side) MA-g-HDPE.

After 24 hours the viscous gel product and supernatant were vacuum dried at 50° C. for 72 hours; due to the complexity of evaporating off DMSO, only the xylenes portion of the supernatant was removed via vacuum drying. The DMSO was removed through hydrolysis process since it is miscible with both $H_2O$ and ethanol.

The amount (g) of HA-CTA and MA-g-HDPE used in the reaction, as determined by amount of the 0.1% (w/v) solution of MA-g-HDPE in xylenes and 0.5% (w/v) solution of HA-CTA in DMSO used in the reaction, can be adjusted to synthesize copolymer products with different theoretical weight percentages of HA and HDPE. The glycosaminoglycan weight percentage of the copolymer was calculated prior to the reaction assuming 100% reaction between constituents and complete substitution of the CTA+ with Na+ during hydrolysis, which determined the required amount of MA-g-HDPE and HA-CTA to be used in the reaction (see, also, Example 2 of Prov. App. No. 60/925,452, section 3.2.2 for general reference).

Using techniques similar to those described above, multiple theoretical weight percentages (40-98%) of the glycosaminoglycan to polyolefin, in the novel amphiphilic copolymer, were fabricated in order to observe the effects of different weight percentages of the glycosaminoglycan. The copolymer was also fabricated from glycosaminoglycans with various molecular weights (640 kDa and 1.5 Da) and functionalized polyolefins with various anhydride graft (i.e., weight) percentages (0.3 and 3.0%) and various molecular weights (15 kg/mol and 121.5 kg/mol). Chemical crosslinking of the glycosaminoglycan portion of the graft copolymer (see, also, FIG. 6 of PCT/US2008/005054 at 28) was accomplished via a poly(hexamethylene diisocyanate) crosslinker after hydrolysis.

To determine if the graft copolymer and the crosslinked graft copolymer powders could be compression molded, powder was placed in a stainless steel mold (such molds are commonplace, and can be shaped with a cylindrical inner cavity for molding the material in compression). The compression molding cycles for both the graft copolymer and the crosslinked (XL) graft copolymer were identical; refer to FIG. 3(b) of PCT/US2008/005054, also labeled in Example 2 of Prov. App. No. 60/925,452 as FIG. 3.4: "Compression molding cycle for HA-co-HDPE and XL HA-co-HDPE specimens (85 and 98 weight % HA)" depicting how temp and pressure varied over time. The melt soak temperature was approximately 10-15° C. above the average melt temperature of the graft copolymer, which was deduced from differential scanning calorimetry results.

The reaction between the modified glycosaminoglycan and the anhydride graft polyethylene was carried out in an inert atmosphere, forming the novel graft copolymer. FIG. 2 of PCT/US2008/005054 depicts a reaction test set-up configuration for Example 1 graft copolymer synthesis. The reaction yields were approximately 95%. The resulting product was a swollen gel network (encapsulating the non-aqueous solvents) for higher weight percents of HA and was a melt-processable powder for lower weight percents of HA. A white, fluffy, porous powder was generated via hydrolysis, in which modified glycosaminoglycan graft copolymer converted to an unmodified glycosaminoglycan graft copolymer. FIG. 3 of PCT/US2008/005054 is a scanning electron microscopy (SEM) image of the converted graft copolymer in powder form (FIG. 6 of PCT/US2008/005054, box 26).

Upon hydration with water, the graft copolymer behaved like a hydrogel; the liquid prevented the polymer network (i.e. physically and chemically crosslinked mesh made up of polymer chains) from collapsing into a compact mass, and the network retained the liquid. The non-crosslinked graft copolymer was completely dispersed, but not dissolved, in water at room temperature after several hours; the crosslinked graft copolymer behaved qualitatively similar to the non-crosslinked graft copolymer. The graft copolymers both dispersed, but did not dissolve, in either or xylenes at room temperature. The insolubility of the copolymer indicates that a reaction did take place to form covalent bonds between the water soluble HA and xylenes soluble HDPE. The insoluble nature of the unique copolymer poses a challenge when attempting to characterize the graft copolymer and crosslinked graft copolymer using standard, conventional analytical techniques. Both a graft copolymer that is unmodified and a crosslinked graft copolymer are not soluble in any typical organic solvent, which hinders the use of solution dependent polymer characterization methods. The lack of solubility precludes the measurement of molecular weight, for example.

Figure 4:
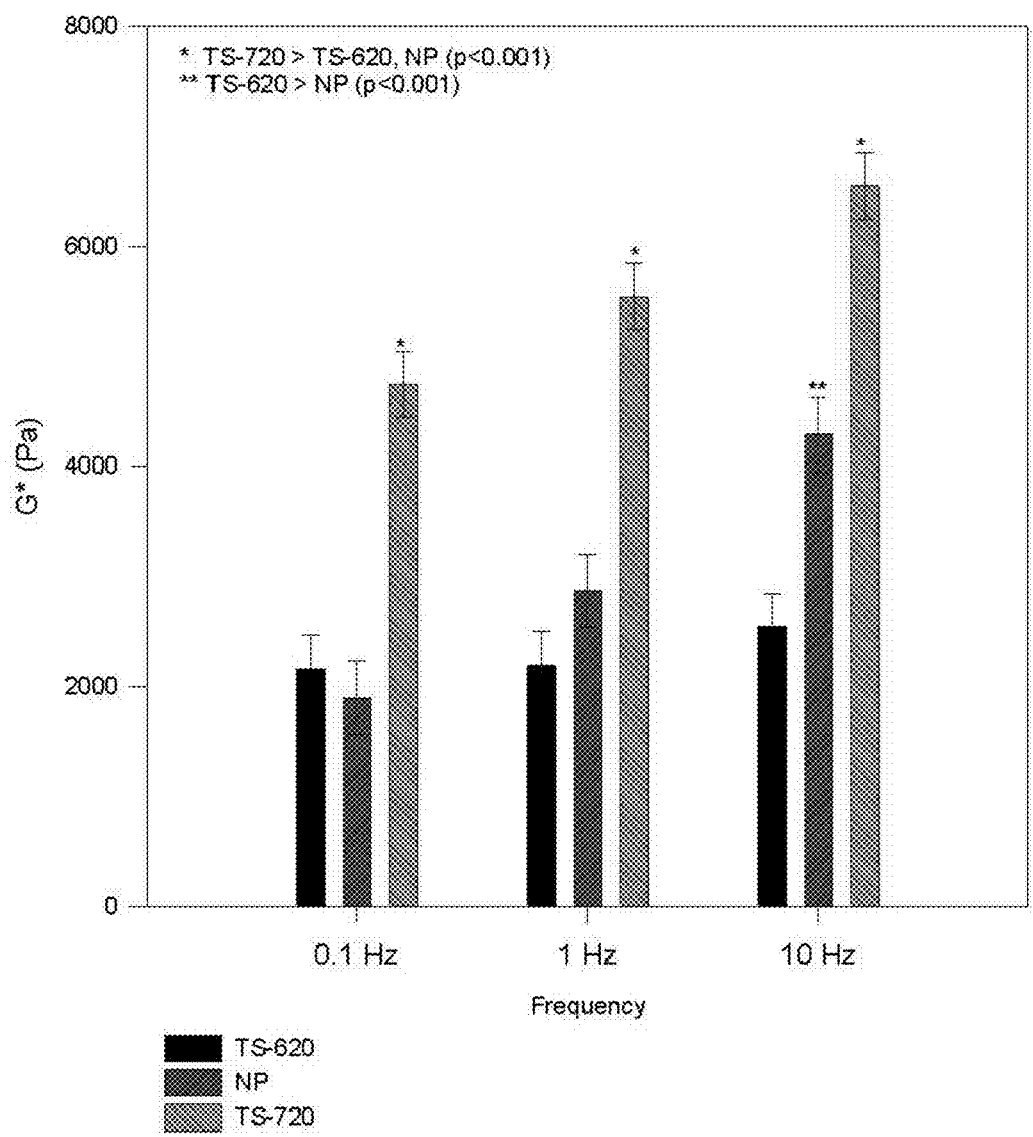
FIG. 4 is a graph showing complex shear moduli for silica-reinforced 95:5 CoPEMA gels (TS-620 and TS-720, n=6 per group) and ovine nucleus pulposus (NP, n=5)

FIG. 4(a) of PCT/US2008/005054 graphically depicts results from a differential scanning calorimetric scan overlay of anhydride graft polyethylene (refluxed MA-g-HDPE; 0.3% MA, 121.5 kg/mol), the glycosaminoglycan (HA; 1.5 MDa), and various graft copolymers with specific glycosaminoglycan weight percentages (10 molar=85% HA, 1 molar=98% HA). FIG. 4(b) of PCT/US2008/005054 graphically depicts results from a differential scanning calorimetric scan of HA-co-HDPE fabricated from MA-g-HDPE with a molecular weight of 15 kg/mole (50% HA). The introduction of HA lowered the melt temperature (peak temperature value) and percent crystallinity (peak area) of the anyhydride graft polyethylene. The changes in the peak values and areas, representing changes in the crystalline domains of the copolymer compared to the two constituents indicate covalent bonding between the HA to MA-g-HDPE (i.e., indicate copolymer formation). As described above, the melt temperature of the different graft copolymers was used to develop the compression molding cycle for the graft copolymers.

Thermogravimetric analysis scans were also analyzed and the degradation temperature of each polymer was determined: FIG. 5 of PCT/US2008/005054 graphically depicts results from a thermal gravimetric analysis scan of the graft copolymer, a blend of the anhydride graft polyethylene and glycosaminoglycan (MA-g-HDPE and HA), and its constituents. The TGA scans show that the esterification reaction between HA and HDPE affects the degradation profiles of the two constituent polymers, verifying covalent bond formation between HA and MA-g-HDPE in the copolymer. From the thermogravimetric analysis data, the experimental weight percentages of the constituents can be compared to theoretical weight percentage calculations performed prior to the reaction taking place. Table 1 compares the values for theoretical and experimental weight percentages.

TABLE 1

Comparison Between Theoretical Constituent Weight Ratios and the Weight Ratios Calculated from TGA Data for HA-co-HDPE

| Theoretical HA:HDPE | TGA HA:HDPE |
|---|---|
| 30:70 | 42:53 |
| 40:60 | 37:50 |
| 50:50 | 33:67 |
| (HA, 1.4 × 10$^6$ Da) | |

TABLE 1-continued

Comparison Between Theoretical Constituent Weight Ratios and
the Weight Ratios Calculated from TGA Data for HA-co-HDPE

| Theoretical<br>HA:HDPE | TGA<br>HA:HDPE |
|---|---|
| 50:50<br>(HA, 6.4 × 10$^5$ Da) | 35:65 |
| 60:40<br>(HA, 1.4 × 10$^6$ Da) | 56:44 |

To further verify that the resultant copolymer was the product of the anhydride graft polyethylene and the HA-CTA, two negative control (also referred to as 'sham') reactions were performed. The first sham/control reaction was run, exactly as described above, but with plain high density polyethylene (HDPE) in the place of the anhydride graft polyethylene. In other words, in the absence of air and water, plain HDPE was refluxed in xylenes at ~145° C. and then added to the HA-CTA in DMSO at ~80° C.

A second sham/control reaction was carried out between anhydride graft polyethylene in xylenes and DMSO with no HA-CTA.

Neither sham/control reaction formed a copolymer. The sham reactions did not form a gel product as occurs with the anhydride polyethylene/HA-CTA reaction according to the processes depicted in FIGS. 6 and 7 of PCT/US2008/005054. When the solvents were evaporated, two distinct phase-separated powders remained from the first sham reaction and a single powder (anhydride graft polyethylene) remained from the second sham reaction. In other words, no copolymer was formed.

The non-degradable hydrophobic portion of the novel copolymer may also be chemically crosslinked via irradiation (gamma or e-beam), silane or peroxides (e.g. dicumyl peroxide [(bis(1-methyl-1-phenylethyl) peroxide], and benzyl peroxide [2,5-Dimethyl-2,5-di-(tert-butyl-peroxy) hexyne-3 peroxide], 2,5-dimethyl-2,5-bis(tert-butylperoxy)-3-hexyne), which would serve to increase the mechanical properties of the graft copolymer and alter the physical (rheological) properties of the graft copolymer.

Example 2

HA-Co-PEMA Hydrogel Synthesis

One embodiment of the HA-co-PEMA hydrogel of the present invention was synthesized according to the protocol presented below.

Determine the dry weight of reactants (HA-CTA and PEMA) for the desired formulation based upon the reactant weight ratio (see Table 2).

TABLE 2

Copolymer Formulation Weight Ratios

| Internal<br>Nomenclature | Reactant Weight Ratio<br>HA-CTA:PEMA |
|---|---|
| 99:1 CoPEMA | 36:1 |
| 95:5 CoPEMA | 7:1 |
| 85:15 CoPEMA | 2:1 |
| 70:30 CoPEMA | 4:5 |
| 5:95 CoPEMA | 1:20 |

For example, approximately 1 g of a 95:5 gel formulation (unhydrolyzed) will require ⅞ g HA-CTA and ⅛ g PEMA.

Weigh a slight excess of reactants (to allow for weight loss due to the evaporation of water) and place into separate labeled containers. Vacuum dry reactants at 50° C. and −25 inches Hg for a minimum of 24 hours. Place glassware to be used for the reaction in a 100° C. oven. Note: Exposure to water will hydrolyze the maleic anhydride and reduce the reactivity of the PEMA. Vacuum drying will close the anhydride rings and reactivate the MA functional groups.

Copolymerization Reaction:

Place HA-CTA in 500 ml RBF along with an appropriate stir bar. Spread vacuum grease on two rubber serum stoppers and place stoppers in side necks of the flask. Secure stoppers with copper wire and parafilm. Attach condenser to middle neck of RBF, using vacuum grease or teflon sleeve to seal. Wrap connection with parafilm and secure with Keck clip. Add DMSO via cannula under dry N$_2$ flow, forming ~0.5% w/v solution (for 1.6 MDa HA; higher concentrations can be used for smaller HA). Continue to flush the system for a few minutes after the appropriate volume of DMSO has been added, closing off the system with a slight positive pressure of dry N$_2$. Heat to 80° C. in an oil bath and stir vigorously for four hours to dissolve all HA-CTA. Place PEMA and appropriate stir bar in 250 ml RBF. Seal flask and add DMSO as described above for HA-CTA to form a 0.1% w/v concentration. Heat to 80° C. under vigorous stirring in an oil bath until PEMA goes into solution, approximately two hours. Once the HA-CTA and PEMA have gone into solution, raise the temperature for the HA-CTA/DMSO flask to 90° C. Transfer the PEMA-DMSO solution to the 500 ml RBF via cannula under N$_2$ flow. Mix the two solutions, stirring vigorously, for 12 hours at 90° C.

Copolymer Processing:

Process reaction product per a CoPEMA Crosslinking protocol (see Example 4) or a Copolymer Washing protocol (see Example 5).

Example 3

Tripolymer Hydrogel Synthesis

Calculate the dry weight of reactants (HA-CTA, PEMA, and PE-g-MA) for the desired formulation based upon the reactant weight ratio (see Table 3):

TABLE 3

Copolymer Formulation Variations

| Internal<br>Nomenclature | Reactant Weight Ratio<br>HA-CTA:PEMA |
|---|---|
| 85:10:5 Tripoly | 27.2:8.7:1* |
| 70:15:15 Tripoly | 7.5:4.4:1* |

Weigh a slight excess of reactants (to allow for weight loss due to the evaporation of water) and place into separate labeled containers. Vacuum dry reactants at 50° C. and −25 inches Hg for a minimum of 24 hours. Place glassware to be used for the reaction in a 100° C. oven. Note: Exposure to water will hydrolyze the maleic anhydride and reduce the reactivity of the PEMA. Vacuum drying will close the anhydride rings and reactivate the MA functional groups.

Copolymerization Reaction:

Place HA-CTA in 500 ml RBF along with an appropriate stir bar. Spread vacuum grease on two rubber serum stoppers and place stoppers in side necks of the flask. Secure stoppers with copper wire and parafilm. Attach condenser to middle neck of RBF, using vacuum grease or teflon sleeve to seal.

Wrap connection with parafilm and secure with Keck clip. Add DMSO via cannula under dry $N_2$ flow, forming ~0.5% w/v solution (for 1.6 MDa HA; higher concentrations can be used for smaller HA). Continue to flush the system for a few minutes after the appropriate volume of DMSO has been added, closing off the system with a slight positive pressure of dry $N_2$. Heat to 80° C. in an oil bath and stir vigorously for four hours to dissolve all HA-CTA.

While HA-CTA is stirring, prepare PE solution: Place PEMA and appropriate stir bar in 250 ml RBF. Seal flask and add DMSO as described above for HA-CTA to form a 0.1% w/v concentration. Heat to 80° C. under vigorous stirring in an oil bath. Place PE-g-MA and an appropriate volume of TCB to form a 0.1% w/v concentration in a 250 ml RBF. Add stir bar and seal flask as described above. Attach to condenser and flush with dry $N_2$ for a few minutes. Heat to 80° C. under vigorous stirring in an oil bath. Once both PE mixtures have gone into solution (approximately two hours), transfer the PEMA solution to the PE-g-MA flask. Allow to mix vigorously for two hours. Once the HA-CTA has gone into solution and the PE mixture is well entangled, raise the temperature for the HA-CTA/DMSO flask to 90° C. Transfer the PEMA-DMSO solution to the 500 ml RBF via cannula under $N_2$ flow. Mix the two solutions, stirring vigorously, for 12 hours at 90° C.

Copolymer Processing:

Process reaction product per a CoPEMA Crosslinking protocol (see Example 4) or a Copolymer Washing protocol (see Example 5).

Example 4

CoPEMA Crosslinking

Combine the coPEMA reaction product and an excess volume (3-4×) of a non-solvent (e.g., acetone, xylenes) in a large beaker to form a "gel" precipitate. Acetone can be used for high HA content; xylenes for mid to high PEMA content. Cover and soak for a minimum of 4 hours. Filter solvents from the gel using a Buchner funnel and vacuum flask. Wash and filter gel precipitate with acetone three times (may be increased). Resuspend the copolymer in a small volume of DMSO; mix vigorously using a vortexer. Add HMDI for a final concentration of up to 5% v/v with the DMSO and cast the suspension into a vial or petri dish as appropriate for desired shape. Allow the suspension to cure at room temperature for a minimum of 24 hours. Soak the crosslinked gel in several changes of acetone to remove excess HMDI. Prepare a 0.2M NaCl aqueous hydrolyzing solution. Immerse the crosslinked gel in the hydrolyzing solution and gently agitate (e.g. in shaker oven) at room temperature overnight.

Example 5

Washing Protocol

Prepare a 0.2M NaCl aqueous hydrolyzing solution (volume greater than the reaction volume) in a large beaker or flask. Add the copolymer suspension (HA-co-HDPE, HA-co-PEMA, tripolymer) to the hydrolyzing solution and mix at room temperature overnight. Add an excess of chilled EtOH and mix for a minimum of four hours to precipitate the copolymer. Allow to stand at room temperature; copolymer will begin to settle at the bottom of the beaker/flask. Centrifuge for 10 minutes to begin separating precipitate from supernatant. Filter supernatant using a ceramic filter and vacuum flask; soak precipitate pellets in isopropyl alcohol. Wash and filter precipitate with isopropyl alcohol three times (may be increased). Resuspend the copolymer in a small volume of distilled $H_2O$; mix at room temperature for four hours. Re-precipitate with an excess of isopropyl alcohol, mixing again at room temperature for four hours. Allow the solution to stand at room temperature; filter and wash as described above. Vacuum dry the HA-co-PEMA at −25 inches Hg overnight or until there is no change in weight.

Example 6

Preliminary Swell Tests for Crosslinked HA-Co-PEMA Hydrogels in Deionized Water Swell tests were conducted for various crosslinked HA-co-PEMA hydrogels in deionized water. HA-co-PEMA gels were crosslinked with 1% (Hydrogel #1), 2.5% (Hydrogel #2), and 5% (Hydrogel #3) v/v crosslinking solutions. To calculate swell ratio (Q), dry hydrogel samples (n=3 per group) are immersed in solvent (here, deionized water (DI)) and allowed to swell at room temperature. The weight of the swollen hydrogels is monitored until equilibrium swelling is achieved. Equilibrium is determined by three consecutive measurements with no further weight gain. The swelling ratio (Q) is determined as follows:

$$Q = \frac{(W_s - W_d)}{W_d},$$

where Q is the swelling ratio, $W_s$ is the swollen weight (which can also be referred to as the wet weight), and $W_d$ is the dry weight. The weight percentage of solvent (here, DI water), (H), is also determined:

$$H = \frac{(W_s - W_d)}{W_s} \times 100\%$$

The results of these tests are shown below in Table 4:

TABLE 4

Preliminary Swell Test Results for Crosslinked HA-co-PEMA Hydrogels in Deionized Water

|  | Hydrogel #1 | Hydrogel #2 | Hydrogel #3 |
| --- | --- | --- | --- |
| % HMDI (v/v) | 1% | 2.5% | 5% |
| Swell ratio (Q) ((wet − dry)/dry) | 152.6 | 57.1 | 33.3 |
| % water content ((wet − dry)/wet) | 99.3% | 98.2% | 96.9% |

HMDI = hexamethylene diisocyanate, a chemical crosslinker

Figure 1:
FIG. 1 is a photograph of three samples of crosslinked HA-co-PEMA stained gels suspended in deionized water. The gels were stained with toluidine blue O to highlight hyaluronan content. From left-to-right, the gels were crosslinked with 1%, 2.5%, and 5% v/v crosslinking solutions.

FIG. 1 illustrates the stained gels suspended in deionized water, with the vials from left-to-right corresponding to gels crosslinked with 1% (Hydrogel #1), 2.5% (Hydrogel #2), and 5% (Hydrogel #3) v/v crosslinking solutions. The gels were stained with toluidine blue to indicate HA content.

As shown in Table 4, in some embodiments, the polymeric material and/or hydrogels according to the invention have a swell ratio (Q) of 33.3 to 152.6 (e.g., 33.3, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, or 152.6), including any and all ranges and subranges therein (e.g., 33.3 to 57.1, 33.3 to 125, 33.3 to 115, 33.3 to 110, 33.3 to 100, etc.).

In some embodiments, the polymeric material and/or hydrogels according to the invention have a swell ratio (Q) of 15 to 125 (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125), including any and all ranges and subranges therein (e.g., 25 to 125, 30 to 120, etc.).

In some embodiments, the polymeric material and/or hydrogels according to the invention have a swell ratio (Q) of less than 125, less than 115, less than 110, or less than 100.

Example 7

HA-Co-PEMA Cast Gel Synthesis

One embodiment of the HA-co-PEMA hydrogel of the present invention was synthesized according to the protocol presented below.

Materials & Equipment:

The following is a list of materials and equipment that were used to synthesize one embodiment of the polymeric material and hydrogel of the present invention: Hyaluronan-cetyl trimethylammonium complex (HA-CTA); Poly(ethylene-alt-maleic anhydride) (PEMA); Dimethyl sulfoxide (DMSO); Qty. 2 two-necked round-bottomed flasks (RBF); Serum stoppers; Copper wire; Keck clips; Condensers; $N_2$ (dry) gas; Oil bath; Weigh boat(s); Analytical scale; Magnetic stir bar(s); Stir plate(s); 70×50 crystallizing dish; Reinforcing agents (optional) (e.g., Particulate reinforcement: Cab-o-Sil fumed silica, TS-620/TS-720 (Cabot, Boston, Mass.)) (e.g., Fibrous reinforcement: Carbon nanotubes (nanotubes or nanofibers), Chitosan nanofibers); Disposable pipettes, 25 ml and 1 ml; Forceps; Pipette aid or bulb pipette; Vacuum bags and sealer; Disposable glove box (Sigma Aldrich); Temperature-controlled oven, e.g. Shake'n Bake Hybridization Oven; Ultrasonic bath; Acetone; NaCl; Deionized water; Ethanol (EtOH); and Vacuum oven.

Procedure:

The following are procedures that were used to synthesize one embodiment of the polymeric material and hydrogel of the present invention:

Stock Solutions: Note: Allow a minimum of 1 day prior to gel casting for preparation of stock solutions. Precautions for air/water-sensitive chemistry should be observed, i.e. HA-CTA and PEMA powders should be vacuum dried a minimum of 24 hours prior to use, glassware should be stored at 100° C. to ensure it is completely dry, stir bars should be rinsed with acetone before use.

Prepare a concentrated solution of HA-CTA in DMSO, aiming for a viscosity similar to honey. A 2.5% w/v concentration is appropriate for HA-CTA prepared from HA in the 450-500 kDa size range. The procedure is as follows: Weigh HA-CTA and place along with stir bar in an appropriately-sized RBF. Seal side neck of RBF with a serum stopper secured with copper wire. Attach RBF to condenser with a Keck clip, lower into oil bath, set temperature to 80° C. and begin stirring. Insert vent needle and transfer canula into rubber serum stopper. Transfer appropriate volume of DMSO (100 ml for every 2.5 g HA-CTA) into flask via canula under $N_2$ flow. Flush flask with $N_2$ by plugging vent, allowing slight positive pressure to build, and releasing plug a total of 3 times; plug vent and remove along with canula, leaving slight positive pressure of $N_2$ in the flask. When HA-CTA is fully dissolved (can take 12+ hours) remove from heat and allow to come to room temperature.

Prepare a 10% w/v concentrated solution of PEMA in DMSO, following procedure described above for HA-CTA solution. The PEMA will go into solution much more readily than the HA-CTA and thus will not need to be on heat for as long.

Gel Casting: Note: This reaction is air/water sensitive. If available, work inside a glove box filled w/dry nitrogen, sealing the cast gel into a vacuum bag prior to removal from the glove box. If a glove box is not available, air/water contact can be minimized by working with sealed vacuum bags as described below.

Base formulation: 16.5 ml 2.5% (w/v) HA-CTA in DMSO; 0.6 ml 10% (w/v) PEMA in DMSO.

Reinforcement (optional): 0.8 g treated silica (Cabot TS-620 or TS-720) max or fibrous reinforcement (e.g. carbon nanotubes, chitosan nanofibers).

Measure PEMA solution into a vial and seal with a serum stopper and copper wire. Flush vial with $N_2$ gas.

Measure HA-CTA solution into 70×50 crystallizing dish using 25 ml serological pipette. If reinforcement is to be used, add and stir by hand at this time. Place appropriately-sized stir bar into dish, then place dish and a pair of forceps into a large vacuum bag modified with a serum-stopper "port"; remove air with vacuum and flush with $N_2$ gas three times. Omit vacuum bag if working in glove box.

Place crystallizing dish on stir plate; turn-on stir plate to start mixing. Slowly add PEMA solution to the stirring HA-CTA solution via canula and low $N_2$ flow (if using vacuum bag) or dropwise using a pipette (if working in a glove box). The HA-CTA and PEMA solutions should complex, becoming more viscous. This may necessitate moving the dish around on the plate and adjusting the stir plate r.p.m. to get good mixing.

Remove the stir bar from the dish using the forceps. If working in a glove box, place the cast gel into a vacuum bag and seal immediately upon removal from glove box. Otherwise, push the forceps and stir bar to one end of the vacuum bag and re-seal the vacuum bag around the forceps and stir bar; cut bag to remove.

Place sealed dish into 75° C. oven to cure for 24 hours.

After curing, remove excess PEMA by sonication with acetone for 30 minutes. Flip gel and repeat.

Prepare a 0.2M NaCl aqueous hydrolyzing solution in a large beaker or flask. Add the hydrolyzing solution to the crystallizing dish and sonicate for 30 minutes.

Replace hydrolyzing solution with deionized water and repeat sonication for 30 minutes. The gel will swell to a greater extent in deionized water, allowing trapped NaCTA to be removed. Repeat the sonication if the solution appears to be "soapy."

Dehydrate gel by soaking in ethanol a few hours or overnight; drain ethanol and completely dry in a vacuum oven at equipped with a solvent trap at −25 inches Hg until there is negligible change in weight.

Example 8

Synthesis of a Hyaluronan-Polyethylene Copolymer Hydrogel for Orthopedic Repair Abstract: Hyaluronan-high density polyethylene graft copolymer (HA-co-HDPE, or Copoly) has previously been synthesized from hyaluronan (HA), a glycosaminoglycan, and high density polyethylene (HDPE), a synthetic plastic. HA-co-HDPE combines the mechanical properties of polyethylene with the lubricating benefits of hyaluronan; due to its biocompatibility, it may be a promising material for meniscal cartilage replacement or injectable nucleus pulposus repair. The following study attempts to improve upon the chemistry of the original reaction in order to synthesize a hyaluronan-polyethylene copolymer that behaves as a true hydrogel.

Introduction:

Biocompatible hydrogels serve as practical materials in orthopedic medicine. A true hydrogel network will swell and preserve structural integrity in a water or saline environment, which are advantageous properties for materials used in orthopedic replacements or repair. An ideal hydrogel for such applications would feature both the mechanical strength of polyethylene (PE), a plastic used in artificial joints, and the lubricating character of hyaluronan (HA), the "gooey" or viscous glycosaminoglycan found throughout the body, including in synovial fluid and around articular cartilage. Previous studies[1] synthesized an HA-PE copolymer (HA-co-PE) from ammonium cation-complexed HA and maleated PE, via esterification reactions between the primary hydroxyls of the HA chain and maleic anhydride (MA) groups grafted onto the polyethylene backbone. However, this original HA-co-PE lacked mechanical integrity when swollen in water. The objective of this research was to synthesize a hyaluronanpolyethylene copolymer that behaves as a true hydrogel.

Hyaluronan is a hydrophilic glycosaminoglycan found in synovial fluid and coating articular cartilage, known for its lubricating properties. The structure of hyaluronan is well known.

Polyethylene is a hydrophobic durable thermoplastic often used in artificial joints. The structure of polyethylene is well known.

Several approaches are described here. The original copolymer reaction was repeated, replacing 1,2,4-trichlorobenzene for xylenes as a more DMSO-miscible solvent in order to increase the reactive interface. An HA amide reduction experiment was also conducted in an attempt to functionalize HA with crosslinker-compatible primary amine reactive groups. Finally and most promisingly, a collection of copolymers with varying ratios of PE-g-MA, PE-alt-MA, and HA-CIA, were synthesized, crosslinked, and characterized by swell tests and FTIR.

CopolyGel: PE-Alt-MA and HA-CTA

The maleic anhydride to hydroxyl (MA:OH) reactive ratio of the Copoly reaction is 1:185; that is, the hydroxyl is in extreme excess. In order to optimize the molar ratio, a polyethylene incorporating more maleic anhydride groups is ideal. For this purpose poly(ethylene-alternating-maleic anhydride), comprised of 78% maleic anhydride by weight, was chosen to replace polyethylene-graft-maleic anhydride, which featured only 3% maleic anhydride by weight, leaving OH in great excess and limiting the number ester linkages. In the case of an 85:15 HA:PE final product ratio, this shifts the reactive ratio to 1:1.58, in favor of MA (the "perfect" ratio is 1:4, since HA contains four hydroxyl groups, only one of which is primary and thus reactive).

The esterification reaction between maleated polyethylene and HA-CTA is as shown in Scheme 1 (provided above).

PE-alt-MA, unlike PE-g-MA, is actually a copolymer with an alternating ethylene-MA-ethylene-MA structure. Without a polyethylene backbone, PE-alt-MA may not behave like true polyethylene. In fact, PE-alt-MA is water-soluble, while polyethylene and PE-g-MA are hydrophobic; PE-alt-MA is also soluble in DMSO. This allows the copolymer esterification reaction to occur in only DMSO, eliminating the need for a second solvent (xylenes or TCB) and expanding the reaction interface to the entire volume of solution. However, the dissimilarity of its physical properties also suggests that PE-alt-MA may not provide the strength or durability of polyethylene, since it cannot form the random crystalline segments that provide polyethylene its characteristic strength, and any network it forms with HA could potentially lack necessary mechanical integrity.

The structures of (a) a polyethylene backbone with grafted maleic anhydride groups and (b) an alternating ethylene-maleic anhydride copolymer are provided hereinabove.

CopolyGel was synthesized in two formulations, a 85:15 or 70:30 HA:PE final product ratio, so that it could be compared to Copoly materials of similar product composition. PE-alt-MA and HA-CTA were dissolved in DMSO separately, then reacted together at 90° C. for 12 hours. (A single solvent flask reaction yielded similar results, but separate solvent flasks are recommended to ensure homogeneity.) Hydrolysis, precipitation, washing, hydration, and drying steps were followed as according to the Copoly protocol, although isopropanol replaced ethanol as a washing agent but not as a precipitating agent as salt solutions are insoluble in isopropanol.

Both CopolyGel products behaved as hydrogels. 70:30 was stronger than 85:15 as expected by the relative amount of modified polyethylene present, but both swelled significantly in PBS, a saline solution that mimics physiological salt concentration (95.08% water after one hour for 70:30, 93.53% for 85:15) without falling apart. Still, they lacked the desired mechanical strength; the lubricated outer surface easily separated from the rest of the network, and too much agitation or pressure could cause the network to break apart entirely.

HMDI-Crosslinked CopolyGel

The diisocyanate crosslinker HMDI was explored as a potential avenue for increasing networking in CopolyGel. HMDI, or hexamethylenediisocyanate, crosslinks via an alcohol group on hyaluronan, so it can link together stray chains of HA that disrupt the mechanical integrity of the network. It is less toxic than the commonly used HA crosslinker gluteraldehyde, but due to its water sensitivity it cannot be used as an injectable in vivo crosslinker and requires toxic non-aqueous solvents. An ideal crosslinked gel strikes a balance between strength and swelling ability; a more crosslinked network will hold together tightly but may not be able to absorb much water.

Dry CopolyGel networks were soaked in excess 5% (v/v) HMDI/DMSO solution for approximately 20 hours under nitrogen. The samples were transferred to the vacuum oven at 50-70° C. for 2 hours in order to cure the crosslinker, then washed with acetone and dried. The 70:30 CopolyGel swelled significantly in the HMDI solution, while 85:15 did not swell at all; this may be attributable to the possible excess of PE-alt-MA in 70:30. It is likely that the crosslinking solution could not saturate the network and access loose HA strands, which is reflected in the swell tests (85.39% for 70:30 crosslinked, but 95.31% for 85:15 crosslinked, an increase). However, both crosslinked CopolyGels appeared qualitatively more resistant to stress; 70:30 was hardly lubricious and held together incredibly well in PBS. In order to improve crosslinking, a different CopolyGel and HMDI-soluble solvent should be tested, and to optimize swelling ability, future work can use a more dilute HMDI solution and shorten the reaction time. This study utilized aggressive conditions to test the effectiveness of crosslinking.

TripolymerGel: PE-Alt-MA, PE-g-MA, and HA-CTA

While CopolyGel swelled significantly and maintained a network in water, it lacked mechanical strength and cohesion, breaking apart fairly easily under stress. Meanwhile, Copoly featured the might of polyethylene but never successfully behaved as a hydrogel. Thus a new polymer material, TripolymerGel, was synthesized to unite both features and create a sturdy, resilient hydrogel. PE-alt-MA in DMSO and PE-g-MA in TCB were tangled together, effectively functionalizing the graft polyethylene with an abundance of maleic anhydride groups and creating a reactive polyethylene backbone. This new functionalized polyethylene was reacted with HA-CTA; subsequent steps adhered to the Copoly protocol.

Two TripolymerGel compositions (85:10:5 and 70:15:15) were synthesized according to the amount of final HA to PE provided by each reactant, in the ratio HA:PE(from PE-alt-MA):PE(from PE-g-MA). The 85:10:5 material was expected to behave similarly to CopolyGel 85:15 but with additional strength from the small amount of PE-g-MA; in other words, the PE-g-MA would serve to strengthen the hydrogel. The 70:15:15 material was designed such that the PE-alt-MA would act as a compatibilizer, functionalizing the PE-g-MA so that it would be more reactive.

As expected from the final product ratios, 70:15:15 displayed greater mechanical strength than 85:10:5, although both products held together extremely well and swelled significantly in PBS (96.72% for 85:10:5, 94.67% for 70:15:15). The properties of 85:10:5 resembled those of the nucleus pulposus: it was flexible, elastic, durable, and slippery. Meanwhile, 70:15:15 was more reminiscent of cartilage, tough and sturdy with a lubricated outer surface. Unlike the CopolyGel materials, which tended to break apart under stress and gradually lose some of its viscous surface, the TripolymerGel materials withstood both pressure and agitation and did not appear to lose any material.

HMDI-Crosslinked TripolymerGel

Although the TripolymerGels behaved extremely well in PBS, they were HMDI crosslinked to further improve networking. In keeping with the results from CopolyGel crosslinking, the 85:10:5 network did not swell at all in HMDI/DMSO, while 70:15:15 did slightly. Swell tests yielded expected results (94.66% for 85:10:5 crosslinked, 84.36% for 70:15:15 crosslinked). The crosslinked 70:15:15 was noticeably stiffer than the uncrosslinked version, although 85:10:5 felt only marginally tougher after crosslinking. As discussed in CopolyGel crosslinking, better crosslinking and swell results may be achieved with a different solvent, a less concentrated HMDI solution, or a shorter reaction time.

Conclusion:

Of the many approaches described in this paper, crosslinked CopolyGel and the assortment of TripolymerGel materials are the most promising and applicable to a wide range of orthopedic functions. Further work will explore and improve the biocompatibility, swelling and mechanical properties of these hydrogels.

REFERENCES

[1]Kurkowski, R; James, S P (2008). Copolymer synthesized from modified glycosaminoglycan, GAG, and an anhydride functionalized hydrophobic polymer. U.S. Patent No. PCT/US09/05054. Colorado State University, Fort Collins, Colo., USA. [2]Butler, M F; Ng, Y; Pudney, P D. Mechanism and kinetics of the crosslinking reaction between biopolymers containing primary amine groups and genipin. *J Poly Sci* 2003. 41, 3941-3953. [3]Baran, E T; Mano, J F; Reis, R L. Starch-chitosan hydrogels prepared by reductive alkylation cross-linking. *J Mater Sci* 2004. 15, 759-765. [4]Pourjavadi, A; Aghajani, V; Ghasemzadeh, H. Synthesis, characterization and swelling behavior of chitosan-sucrose as a novel full-polysaccharide superabsorbant hydrogel. *J Appl Poly Sci* 2008. 109, 2648-2655. [5]Stern, R; Kogan, G; Jedrzejas, M J; Soltes, L. The many ways to cleave hyaluronan. *Biotech Advances* 2007. 25, 537-557. [6]Tokita, Y; Okamoto, A. Hydrolytic degradation of hyaluronic acid. *Polymer Degradation and Stability* 1995. 48, 269-273. [7]Gu, L; Zhu, S; Hrymak, A N. Acidic and basic hydrolysis of poly(N-vinylformamide). *J Appl Poly Sci* 2002. 86, 3412-3419.

Example 9

Copolymer Formulation Variations

Provided below is a table showing various copolymer formulation variations of the present invention.

TABLE 5

Copolymer Formulation Variations

| Internal Nomenclature | Reactant Weight Ratio HA-CTA:PEMA | Reinforcement Level HA-CTA:other | Comments |
|---|---|---|---|
| 99:1 CoPEMA | 36:1 | — | |
| 95:5 CoPEMA | 7:1 | — | |
| 95:5 XL | 7:1 | — | Crosslinked with HMDI (hexamethylene diisocyanate) |
| 620-reinforced | 7:1 | 1:2<br>1:1<br>5:1 | TS-620 fumed silica (Cabot Corp.); high, med, low reinforcement |
| 720-reinforced | 7:1 | 1:2<br>1:1<br>5:1 | TS-720 fumed silica (Cabot Corp.); high, med, low reinforcement |
| CN-low | 7:1 | 40:1 | Carbon nanotubes, low level of reinforcement |
| CN-high | 7:1 | 4:1 | Carbon nanotubes |
| Chi-reinforced | 7:1 | 40:1 | Chitosan nanofibers |

TABLE 5-continued

Copolymer Formulation Variations

| Internal Nomenclature | Reactant Weight Ratio HA-CTA:PEMA | Reinforcement Level HA-CTA:other | Comments |
|---|---|---|---|
| 85:15 CoPEMA | 2:1 | — | |
| 85:15 XL | 2:1 | — | Crosslinked with HMDI |
| 70:30 CoPEMA | 4:5 | — | |
| 70:30 XL | 4:5 | — | Crosslinked with HMDI |
| 85:10:5 Tripoly | 27.2:8.7:1* | — | * MA-g-HDPE used as $3^{rd}$ reactant |
| 85:10:5 XL | 27.2:8.7:1* | — | * MA-g-HDPE used as $3^{rd}$ reactant; crosslinked with HMDI |
| 70:15:15 Tripoly | 7.5:4.4:1* | — | * MA-g-HDPE used as $3^{rd}$ reactant |
| 70:15:15 XL | 7.5:4.4:1* | — | * MA-g-HDPE used as $3^{rd}$ reactant; crosslinked with HMDI |
| 5:95 CoPEMA | 1:20 | — | Brittle/crumbly texture |

Example 10

Swell Test Results

Provided below is a table showing swell test results of various copolymer formulation variations of the present invention.

Figure 2A:
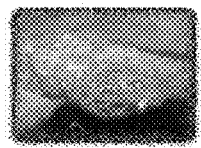
FIGS. 2A-2H are photographs of variations in copolymer formulation, shown swollen in phosphate-buffered saline (PBS), as follows: (A) 85:15 CoPEMA; (B) crosslinked 85:15 CoPEMA; (C) 70:30 CoPEMA; (D) crosslinked 70:30 CoPEMA; (E) 85:10:5 tripolymer gel; (F) 85:10:5 crosslinked tripolymer gel; (G) 70:15:15 tripolymer gel; and (H) 70:15:15 crosslinked tripolymer gel. The samples shown in FIG. 2F and FIG. 2H have been stained with toluidine blue O.
Figure 2B:
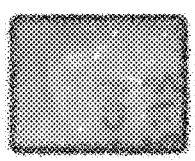
Figure 2C:
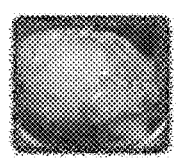
Figure 2D:
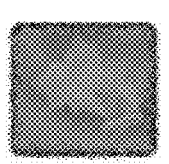
Figure 2E:
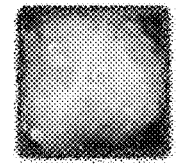
Figure 2F:
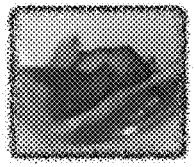
Figure 2G:
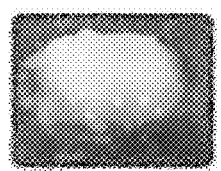
Figure 2H:
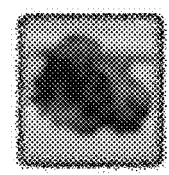
Figure 3:
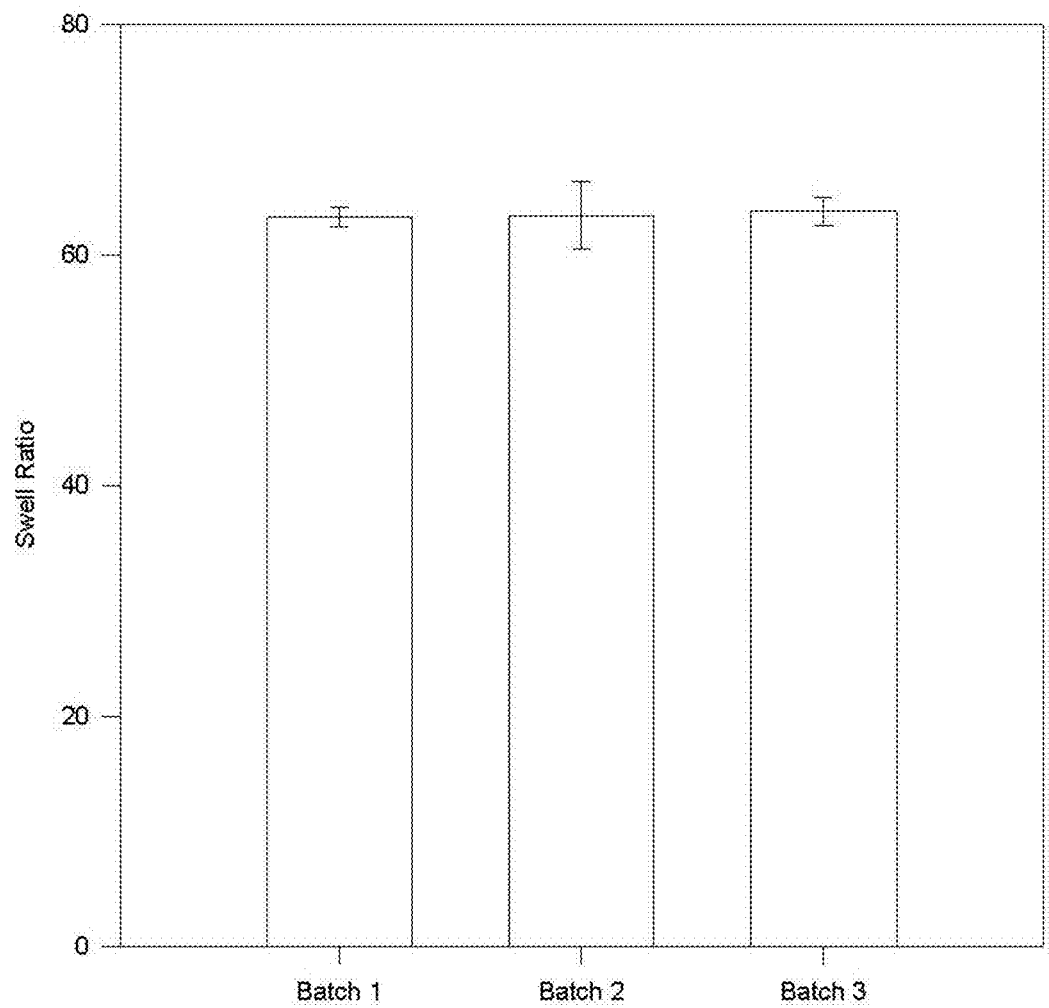
FIG. 3 is a graph showing swell test results for three batches of a "95:5 CoPEMA" formulation (7:1 HA-CTA: PEMA weight ratio). No significant difference is seen among mean equilibrium swell ratios for the three batches (n=3 per group).

| FIG. | Polymer (HA:PE Product Ratio) | Swell Test Water % | Qualitative Properties |
|---|---|---|---|
| FIG. 2A | CopolyGel 85:15 | 93.53 | Viscous, breaks apart with mild agitation or pressure |
| FIG. 2B | CopolyGel 85:15 crosslinked | 95.31 | Viscous, breaks apart with moderate agitation or pressure |
| FIG. 2C | CopolyGel 70:30 | 95.08 | Thick, breaks apart with vigorous agitation |
| FIG. 2D | CopolyGel 70:30 crosslinked | 85.39 | Rubbery, elastic, not lubricious, holds together extremely well |
| FIG. 2E | Tripolymer Gel 85:10:5 | 96.72 | Sturdy, flexible, lubricated surface, like nucleus pulposus |
| FIG. 2F | Tripolymer Gel 85:10:5 crosslinked | 94.66 | Sturdy, flexible, durable, somewhat lubricated surface |
| FIG. 2G | Tripolymer Gel 70:15:15 | 94.67 | Tough, durable, lubricated surface, like cartilage |
| FIG. 2H | Tripolymer Gel 70:15:15 crosslinked | 84.36 | Extremely tough, lubricated surface, holds together well |

As referenced in the above table, FIG. 2A through FIG. 2H are photographs of each polymer hydrogel in PBS solution. Blue gels have been stained with toluidine blue.

Example 11

FTIR Results

FTIR scans were produced for various embodiments of the polymeric material and hydrogels of the present invention, as shown in FIG. 8 through FIG. 10.

As shown in the figures, the FTIR scans indicate the appearance of an ester bond peak (i.e., the covalent bond between the HA and PEMA). In the figures, peaks relating to the ester bond, the base constituents, and the reactive groups have been identified.

Based on the FTIR data, the following conclusions were made with respect to the Tripolymer Gel: (i) strong $CH_2$—OH peak (indicative of HA content); (ii) moderate, sharp C—$H_2$ peaks (indicative of PE content); (iii) indications of desired reaction, including (a) OH peak diminished compared to HA, (b) characteristic peaks for maleic anhydride (C=O, cyclic C—O—C) gone, (c) appearance of moderate —COOH peak, unreacted maleic anhydride hydrolized to maleic acid, and (d) appearance of an ester peak.

Based on the FTIR data, the following conclusions were made with respect to the Co-PEMA: (i) strong OH peak (indicative of HA content); (ii) moderate, broad C—$H_2$ peaks indicative of the small ethylene units in hydrolyzed PEMA; (iii) indications of desired reaction, including (a) OH peak broadened compared to HA, (b) characteristic peaks for maleic anhydride (C=O, cyclic C—O—C) gone, (c) appearance of —COOH peak, unreacted maleic anhydride hydrolized to maleic acid, and (d) appearance of ester peak.

While certain representative embodiments and certain details have been shown for the purpose of illustrating the invention, those skilled in the art will appreciate that various modifications, whether specifically or expressly identified herein, may be made to these representative embodiments without departing from the novel core teachings or scope of this technical disclosure. Accordingly, all such modifications are intended to be included within the scope of the claims. Whether the commonly employed phrase "comprising the steps of" may be used in a method claim, the applicant(s) does not intend to invoke any law in a manner that unduly limits rights to its innovation. Furthermore, in any claim that is filed herewith or hereafter, any means-plus-function clauses used, or later found to be present, are intended to cover at least all structure(s) described herein as performing the recited function and not only structural equivalents but also equivalent structures.

What is claimed is:

1. A polymeric material comprising a tripolymer glycosaminoglycan-polyolefin network, wherein the polymeric material has a swell ratio (Q) in deionized water of less than 125, wherein $$Q = \frac{(W_s - W_d)}{W_d},$$

and wherein $W_s$ and $W_d$ are the weights of the polymeric material at swollen weight and dry weight, respectively, and wherein said tripolymer glycosaminoglycan-polyolefin network is synthesized by reacting a first constituent, a second constituent, and a third constituent with one another in a single phase,
  wherein said first constituent comprises a modified glycosaminoglycan,
  wherein said second constituent comprises an alternating copolymer of a polyolefin with an acid anhydride,
  wherein said third constituent comprises a graft copolymer having a polyolefin backbone functionalized/grafted with an acid anhydride, and
  wherein the first constituent, the second constituent, and the third constituent react to form covalent bonds.

2. The polymeric material according to claim 1, wherein the glycosaminoglycan is selected from the group consisting of hyaluronan, chondroitin sulfates, dermatan sulfates, keratan sulfates, heparan sulfates, and heparin.

3. The polymeric material according to claim 1, wherein the polyolefin in both the second constituent and the third constituent is polyethylene.

4. The polymeric material according to claim 1, wherein the acid anhydride in both the second constituent and the third constituent is maleic anhydride.

5. The polymeric material according claim 1, wherein the first constituent comprises a glycosaminoglycan modified with a paraffin ammonium cation dissociated from a salt selected from the group consisting of alkyltrimethylammonium chloride, alkylamine hydrochloride, alkylpyridinium chloride, alkyldimethylbenzyl ammonium chloride, alkyltrimethylammonium bromide, alkylamine hydrobromide, alkylpyridinium bromide, and alkyldimethylbenzyl ammonium bromide.

6. The polymeric material according to claim 1, wherein the second constituent comprises an alternating copolymer of polyethylene with maleic anhydride.

7. The polymeric material according to claim 1, wherein the second constituent is selected from the group consisting of poly(ethylene-alt-maleic anhydride), poly(styrene-alt-maleic anhydride), poly(isobutylene-alt-maleic anhydride), poly(maleic anhydride-alt-1-octadecene), poly(methyl vinyl ether-alt-maleic anhydride), and derivatives thereof.

8. The polymeric material according to claim 1, wherein the third constituent is selected from the group consisting of maleic anhydride-graft-polyethylene, maleic anhydride-graft-polypropylene, maleic anhydride-graft-polystyrene, polystyrene-graft-maleic anhydride, polyisoprene-graft-maleic anhydride, and polypropylene-graft-maleic anhydride.

9. The polymeric material according to claim 1, wherein the first constituent is hyaluronan, the second constituent is poly(ethylene-alt-maleic anhydride), and the third constituent is maleic anhydride-graft-polyethylene.

10. The polymeric material according to claim 1 further comprising:
a reinforcing agent selected from the group consisting of an inorganic reinforcing agent and an organic reinforcing agent.

11. The polymeric material according to claim 10, wherein the inorganic reinforcing agent comprises an inorganic agent selected from the group consisting of silica, alumina, zirconia, calcium phosphates, and hydroxyapatite.

12. The polymeric material according to claim 10, wherein the organic reinforcing agent is selected from the group consisting of carbon nanotubes, carbon nanofibers, chitosan nanofibers, demineralized bone matrix (DBM), collagen, silk, and cellulose.

13. A hydrogel comprising the polymeric material according to claim 1.

14. The polymeric material according to claim 1, or a hydrogel comprising said polymeric material, having a swell ratio (Q) in deionized water of 15 to 120, wherein $$Q = \frac{(W_s - W_d)}{W_d},$$

and wherein $W_s$ and $W_d$ are the weights of the polymeric material or hydrogel at swollen weight and dry weight, respectively.

15. The polymeric material according to claim 1, or a hydrogel comprising said polymeric material, having a swell ratio (Q) in deionized water of 33.3 to 57.1, wherein $$Q = \frac{(W_s - W_d)}{W_d},$$

and wherein $W_s$ and $W_d$ are the weights of the polymeric material or hydrogel at swollen weight and dry weight, respectively.

16. The polymeric material according to claim 1, or a hydrogel comprising said polymeric material, wherein the polymeric material or hydrogel is non-biodegradable or is resistant to biodegradation.

17. The polymeric material or hydrogel according to claim 16, wherein said material or hydrogel is not susceptible to being decomposed by *Pseudomonas aeruginosa* during a period of at least 15 days.

18. A method of synthesizing a polymeric material comprising a tripolymer glycosaminoglycan-polyolefin network, wherein the polymeric material has a swell ratio (Q) in deionized water of less than 125, wherein $$Q = \frac{(W_s - W_d)}{W_d},$$

and wherein $W_s$ and $W_d$ are the weights of the polymeric material at swollen weight and dry weight, respectively, said method comprising:
providing the following constituents:
(i) a first constituent comprising a modified glycosaminoglycan;
(ii) a second constituent comprising an alternating copolymer of a polyolefin with an acid anhydride; and
(iii) a third constituent comprising a graft copolymer having a polyolefin backbone functionalized/grafted with an acid anhydride; and
reacting the first constituent, the second constituent, and the third constituent in a single phase under conditions effective to yield a tripolymer glycosaminoglycan-polyolefin network,
wherein said tripolymer glycosaminoglycan-polyolefin network comprises the first constituent, the second constituent, and the third constituent covalently bound to one another.

19. The method according to claim 18, wherein the glycosaminoglycan is selected from the group consisting of hyaluronan, chondroitin sulfates, dermatan sulfates, keratan sulfates, heparan sulfates, and heparin.

20. The method according to claim 18, wherein the polyolefin in both the second and third constituent is polyethylene.

* * * * *